(12) United States Patent
Bobrow et al.

(10) Patent No.: US 11,761,955 B2
(45) Date of Patent: Sep. 19, 2023

(54) MULTIPLEXED CATALYZED REPORTER DEPOSITION

(71) Applicant: Ultivue, Inc., Cambridge, MA (US)

(72) Inventors: Mark Bobrow, Lexington, MA (US); Stephanie Rae Hennek, Medford, MA (US); Mael Manesse, Medford, MA (US)

(73) Assignee: Ultivue, Inc., Cambridge, MA (US)

( * ) Notice: Subject to any disclaimer, the term of this patent is extended or adjusted under 35 U.S.C. 154(b) by 983 days.

(21) Appl. No.: 16/433,621

(22) Filed: Jun. 6, 2019

(65) Prior Publication Data
US 2019/0376956 A1 Dec. 12, 2019

Related U.S. Application Data

(60) Provisional application No. 62/760,450, filed on Nov. 13, 2018, provisional application No. 62/682,765, filed on Jun. 8, 2018.

(51) Int. Cl.
| | | |
|---|---|---|
| *G01N 33/535* | (2006.01) | |
| *G01N 33/542* | (2006.01) | |
| *G01N 33/58* | (2006.01) | |
| *G01N 33/543* | (2006.01) | |
| *C12Q 1/6804* | (2018.01) | |

(52) U.S. Cl.
CPC ......... *G01N 33/535* (2013.01); *C12Q 1/6804* (2013.01); *G01N 33/542* (2013.01); *G01N 33/54306* (2013.01); *G01N 33/581* (2013.01); *C12Q 2537/143* (2013.01); *C12Q 2563/125* (2013.01); *G01N 2333/908* (2013.01)

(58) Field of Classification Search
CPC ....... C12Q 1/68; C12Q 1/6804; C12Q 1/6832
See application file for complete search history.

(56) References Cited

U.S. PATENT DOCUMENTS

| | | | |
|---|---|---|---|
| 5,196,306 A | 3/1993 | Bobrow et al. | |
| 5,583,001 A | 12/1996 | Bobrow et al. | |
| 5,731,158 A | 3/1998 | Bobrow et al. | |
| 5,863,748 A | 1/1999 | Bobrow | |
| 6,355,443 B1 | 3/2002 | Bobrow et al. | |
| 7,291,474 B2 | 11/2007 | Bobrow | |
| 9,689,875 B2 | 6/2017 | Smith et al. | |
| 9,874,571 B2 | 1/2018 | Smith et al. | |
| 11,021,737 B2 | 6/2021 | Church et al. | |
| 2006/0228733 A1 | 10/2006 | Pierce et al. | |
| 2017/0226572 A1 | 8/2017 | Armitage et al. | |
| 2019/0317080 A1* | 10/2019 | Campton ............ | G01N 33/581 |

FOREIGN PATENT DOCUMENTS

| | | | |
|---|---|---|---|
| WO | 2006104979 A2 | 10/2006 | |
| WO | 2012112563 A2 | 8/2012 | |
| WO | 2013096851 A1 | 6/2013 | |
| WO | 2014163886 A1 | 10/2014 | |
| WO | 2017143006 A1 | 8/2017 | |
| WO | 2018107054 A1 | 6/2018 | |
| WO | 2018132392 A3 | 8/2018 | |

OTHER PUBLICATIONS

Chu, B.C.F. et al., Ligation of oligonucleotides to nucleic acids or proteins via disulfide bonds, Nucl. Acids Res., vol. 16, pp. 3671-3691 (Year: 1988).*
De Montellano, P.R.O. et al., Mechanism-Based Inactivation of Horseradish Peroxidase by Sodium Azide. Formation of meso-Azidoprotoporhyrin IX, Biochemistry, vol. 27, pp. 5470-5476 (Year: 1988).*
Huang, T.J. et al., An electrochemical detection scheme for identification of single nucleotide polymorphisms using hairpin-forming probes, Nucl. Acids Res., vol. 30, e55, pp. 1-6 (Year: 2002).*
Dirks et al., "Triggered amplification by hybridization chain reaction," PNAS 101(43):15275-15278, 2004.
England et al., "HaloTag Technology: A Versatile Platform for Biomedical Applications," Bioconjugate Chem. 26:975-986 (2015).
Li et al., "Inhibition of Cell Proliferation by an Anti-EGFR Aptamer," PLoS One 6(6):1-10, 2011.
Lizardi et al., "Mutation detection and single-molecule counting using isothermal rolling-circle amplification," nature genetics 19:225-232, 1998.
Zhang, et al., "Automated 5-Plex Fluroescent Immunohistochemistry with Tyramide Signal Amplication Using Unmodified Antibodies from Same Species," Ventana Medical Systems, Inc., Poster, 2015.
Owczarzy et al., "Effects of Sodium Ions on DNA Duplex Oligomers: Improved Predictions of Melting Temperatures," Biochemistry 43:3537-3554, 2004.
Polaske et al., "Quinone Methide Signal Amplication: Covalent Reporter Labeling of Cancer Epitopes using Alkaline Phosphate Substrates," Bioconjugate Chemistry, DOI: 10.1021/acs.bioconjchem.5b00652, pp. 1-8, 2016.
Saka et al., "Highly multiplexed in situ protein imaging with signal amplification by Immuno-SABER," first posted online Dec. 28, 2018; doi: http://dx.doi.org/10.1101/507566, 26 pages.
Shindler et al., "Double Immunofluorescent Staining Using Two Unconjugated Primary Antisera Raised in the Same Species," Journal of Histochemistry and Cytochemistry, 44(11):1331-1335, 1996.
Lin et al., "Highly multiplexed imaging of single cells using a high-throughput cyclic immunofluorescence method," Nat Commun 6:8390, 2015.
Toth et al., "Simultaneous Visualization of Mutliple Antigens with Tyramide Signal Amplication Using Antibodies from the Same Species," Journal of Histochemistry and Cytochemistry 55(6):545-554, 2007.
Xu et al., "Directed Evolution of High-Affinity Antibody Mimics Using mRNA Display," Chemistry & Biology 9:933-942, 2002.
Yin et al., "Programming biomolecular self-assembly pathways," Nature, 451(17):318-323, 2008.
Zhang et al., "Automated 5-plex fluorescent immunohistochemistry with tyramide signal amplification using antibodies from the same species," Journal of Immunotherapy of Cancer 3(Suppl 2):P111, 2015.

(Continued)

*Primary Examiner* — Teresa E Strzelecka
(74) *Attorney, Agent, or Firm* — McNeill Baur PLLC

(57) ABSTRACT

A method for testing a sample for the presence of one or more targets comprises multiplexed catalyzed reporter deposition (CARD) is provided.

14 Claims, 9 Drawing Sheets
(2 of 9 Drawing Sheet(s) Filed in Color)

(56) References Cited

OTHER PUBLICATIONS

Abe et al., "Affinity labeling of vertebrate oxidosqualene cyclases with a tritiated suicide substrate," Biochem Biophys Res Commun 187(3):32-8, 1992.
Manual: Multiplex IHC—Opal(TM) 7 Solid Tumor Immunology Kit available at www.perkinelmer.com/lab-solutions/resources/docs/DTS_OP7TL400TDS.pdf as of Jun. 7, 2019, 10 pages.
Stack et al., "Multiplexed immunohistochemistry, imaging, and quantitation: A review, with an assessment of Tyramide signal amplification, multispectral imaging and multiplex analysis," Methods 70:46-58, 2014.
Alfonta, "Chronopotentiometry and Faradaic impedance spectroscopy as signal transduction methods for the biocatalytic precipitation of an insoluble product on electrode supports: routes for enzyme sensors, immunosensors and DNA sensors," Biosensors & Bioelectronics 16(9-12):675-687, 2001.
International Search Report and Written Opinion issued in International Application No. PCT/US2019/035785, dated Aug. 21, 2019, 16 pages.
Sakharov, "Microplate Chemiluminescent Assay for DNA Detection Using Apoperoxidase-Oligonucleotide as Capture Conjugate and HPR-Streptavidin Signaling System," Sensors 18(4):1-11, 2018.
Wang et al., "Development of Chemiluminescent Lateral Flow Assay for the Detection of Nucleic Acids," Biosensors 2(1):32-42, 2012.

\* cited by examiner

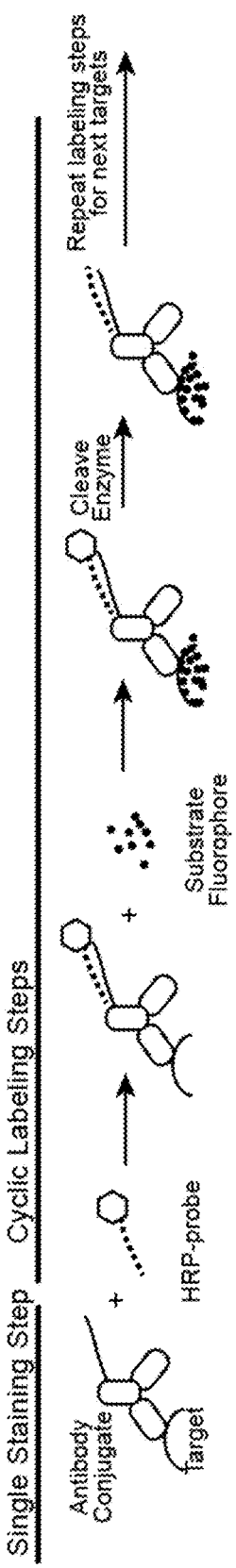
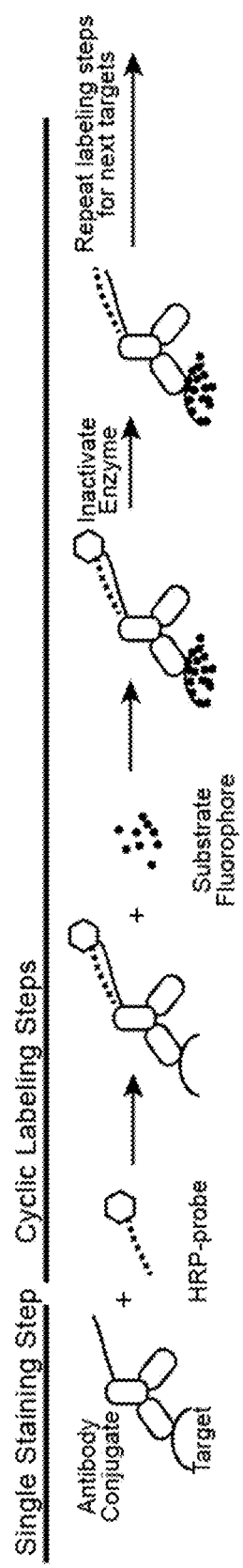
Fig. 4A
Fig. 4B

MULTIPLEXED CATALYZED REPORTER DEPOSITION

CROSS-REFERENCE TO RELATED APPLICATIONS

This application claims the benefit of priority of U.S. Provisional Application No. 62/682,765, filed Jun. 8, 2018, and U.S. Provisional Application No. 62/760,450, filed Nov. 13, 2018, the contents of all of which are incorporated by reference herein in their entirety for any purpose.

FIELD

This application relates generally to the field of detection of analytes (e.g., targets), and in particular, relates to detection methods using catalyzed reporter deposition (CARD).

BACKGROUND

For research and medical applications, it can be desirable to detect multiple biologically relevant molecules within a single cell or tissue sample. Immunological methods are commonly used for this purpose. Such methods generally involve binding antibodies to molecules of interest in the sample, generating detectable signals associated with the antibodies so that each molecule of interested is distinguished from another, and using an analytical method to detect the signals. Catalyzed reporter deposition (CARD) has been used in such immunological methods to generate enhanced signals associated with antibodies. The typical workflow for CARD is to apply a target molecule-specific antibody to a sample, then apply a secondary antibody that recognizes the primary antibody. The secondary antibody is linked to an enzyme (e.g., horse radish peroxidase (HRP), alkaline phosphatase) that converts a substrate into a reactive agent that binds to nearby phenolic residues (e.g., tyrosine). Because phenolic residues are plentiful in cellular samples, the result is dense labeling in the vicinity of the primary antibody.

One technical problem with CARD is difficulty in removing the secondary antibody from the sample. This issue arises when it is desired to probe for additional molecules of interest in the same sample using additional primary antibodies. It is possible to use heat or microwaving to removed secondary antibodies, but this method can damage samples, reducing the quality of subsequent testing. Further, this processing is often time-consuming Therefore, a method that avoids harsh sample treatment and allows detection of multiple molecules of interest in a single sample would be a useful advancement in CARD methodologies.

SUMMARY

In accordance with the description, a method for testing a sample for the presence of one or more targets is provided to multiplex catalyzed reporter deposition (CARD) and to achieve higher levels of multiplexed detection.

In one embodiment, a method for testing a sample for the presence of one or more targets comprises:

(1) contacting a sample being tested for the presence of one or more targets with one or more target-specific binding partners, wherein each target-specific binding partner is linked to a nucleic acid strand and wherein target-specific binding partners of different specificity are linked to different nucleic acid strands;

(2) optionally removing unbound target-specific binding partners;

(3) contacting the sample from step (1) or optionally step (2) with an enzyme linked to a nucleic acid strand complementary to the nucleic acid strand linked to the target-specific binding partner, wherein the following (i) or (ii) or both is met:
  (i) the nucleic acid strand is linked to the target-specific binding partner with a first releasable linker; and
  (ii) the enzyme is linked to the complementary nucleic acid strand with a second releasable linker;

(4) optionally removing unbound enzyme linked to complementary nucleic acid strands;

(5) contacting the sample from step (3) or optionally step (4) with a substrate conjugate comprised of a detectably labeled substrate, where the substrate and detectable label are linked optionally with a third releasable linker;

(6) optionally removing unbound substrate conjugate;

(7) optionally releasing the bound enzyme;

(8) optionally imaging the sample to detect the bound detectable labels; and (9) optionally repeating steps (1)-(8) or any subset thereof and optionally if more than one target-specific binding partner is used, repeating steps (1)-(7) or any subset thereof prior to step (8) of imaging.

In some embodiments, the method further comprises repeating steps (3)-(7) prior to step (8) of imaging.

In some embodiments, in step (5), the substrate conjugate comprised of the detectably labeled substrate reacts with the enzyme to form an activated substrate conjugate, and the activated substrate conjugate binds to a receptor for the activated substrate conjugate. Further, the receptor for the activated substrate conjugate may be present in the sample, which is immobilized on a solid support, resulting in the deposition of the detectable labels.

In another embodiment, the method may further comprise (10) optionally releasing the bound detectable labels after step (8) by releasing the third releasable linker and optionally repeating steps (1)-(10) or any subset thereof.

In some embodiments, the method may further comprise amplifying the nucleic acid strand linked, or a portion thereof, to the target-specific binding partner of step (1). In some embodiments, the amplifying step is performed prior to step (3).

In some embodiments, a method for testing a sample for the presence of one or more targets comprises:

(1) contacting a sample being tested for the presence of one or more targets with one or more target-specific binding partners, wherein each target-specific binding partner is linked to a nucleic acid strand and wherein target-specific binding partners of different specificity are linked to different nucleic acid strands;

(2) optionally removing unbound target-specific binding partners;

(3) contacting the sample from step (1) or optionally step (2) with a first member of a binding pair linked to a nucleic acid strand complementary to the nucleic acid strand linked to the target-specific binding partner, wherein the following (i) or (ii) or both is met:
  (i) the nucleic acid strand is linked to the target-specific binding partner with a first releasable linker; and
  (ii) the first member of the binding pair is linked to the complementary nucleic acid strand with a second releasable linker;

(4) optionally removing unbound first member of binding pair linked to complementary nucleic acid strands;

(5) contacting the sample from step (3) or optionally step (4) with a second member of the binding pair linked to an enzyme optionally with a third releasable linker, and optionally removing unbound second member of the binding pair linked to the enzyme;

(6) contacting the sample from step (5) with a substrate conjugate comprised of a labeled substrate, where the substrate and label are linked optionally with a fourth releasable linker;

(7) optionally removing unbound substrate conjugate;

(8) optionally releasing the bound first or second member of the binding pair;

(9) optionally imaging the sample to detect the bound detectable labels; and

(10) optionally repeating steps (1)-(9) or any subset thereof and optionally if more than one target-specific binding partner is used, repeating steps (1)-(8) or any subset thereof prior to step (9) of imaging.

In some embodiment, the method may further comprise (11) optionally releasing the bound detectable labels after step (9) by cleaving the third releasable linker between the label and the substrate, and optionally repeating steps (1)-(11) or any subset thereof.

In some embodiments, the method may further comprise amplifying the nucleic acid strand, or a portion thereof, linked to the target-specific binding partner of step (1). In some embodiments, the amplifying step is performed prior to step (3).

In some embodiment, a method for testing a sample for the presence of one or more targets comprises:

(1) contacting a sample being tested for the presence of one or more targets with one or more target-specific binding partners, wherein each target-specific binding partner is linked to a nucleic acid strand and wherein target-specific binding partners of different specificity are linked to different nucleic acid strands;

(2) optionally removing unbound target-specific binding partners;

(3) contacting the sample from step (1) or optionally step (2) with an enzyme linked to a nucleic acid strand complementary to the nucleic acid strand linked to the target-specific binding partner, wherein the following (i) or (ii) or both is met:

(i) the nucleic acid strand is linked to the target-specific binding partner with a first releasable linker; and
(ii) the enzyme is linked to the complementary nucleic acid strand with a second releasable linker;

(4) optionally removing unbound enzyme linked to complementary nucleic acid strands;

(5) contacting the sample from step (3) or optionally step (4) with a substrate conjugate comprised of a nucleic acid strand-bound substrate, where the substrate and nucleic acid strand are linked optionally with a third releasable linker;

(6) optionally removing unbound substrate conjugate;

(7) optionally releasing the bound enzymes;

(8) contacting the sample from step (5) or optionally steps (6)-(7) with a nucleic acid strand-bound detectable label, linked optionally with a fourth releasable linker, where the nucleic acid strand is a specific binding pair member to the nucleic acid strand in step (5);

(9) optionally imaging the sample to detect the bound labels;

(10) optionally releasing the bound label from step (8); and

(11) optionally repeating steps (1)-(10) or any subset thereof and optionally if more than one target-specific binding partner is used, repeating steps (1)-(8) or any subset thereof prior to step (9).

In some embodiments, the bound label is released with use of a releasable linker. In some embodiments, in step (10), the bound label is released by cleaving the releasable linker of step (5) or optionally step (8) or optionally steps (5) and (8). In some embodiments, the bound label is released without use of a releasable linker. In some embodiments, the bound label is released by dehybridization of the nucleic acid strands. In some embodiments the bound label is released by dehybridization of the nucleic acid strand from step (8) bound to the nucleic acid strand from step (5).

In some embodiments, the method may further comprise amplifying the nucleic acid strand (or a portion thereof) linked to the target-specific binding partner of step (1). In some embodiments, the amplifying step is performed prior to step (3).

In some embodiments, the method may further comprise amplifying the nucleic acid strand (or a portion thereof) of the nucleic acid strand-bound substrate of step (5). In some embodiments, the amplifying step is performed after step (5) or optional step (6) or optional step (7).

In some embodiments, the method may further comprise first amplifying the nucleic acid strand (or a portion thereof) linked to the target-specific binding partner of step (1) and second amplifying the nucleic acid strand of the nucleic acid strand-bound substrate of step (5). In some embodiments, the first amplifying step is performed prior to step (3); and the second amplifying step is performed after step (5) or optional step (6) or optional step (7).

In some embodiments, a method for testing a sample for the presence of one or more targets comprises:

(1) contacting a sample being tested for the presence of one or more targets with one target-specific binding partner, wherein the target-specific binding partner is linked to a nucleic acid strand, (2) optionally removing unbound target-specific binding partners, (3) contacting the sample with an HRP-bound nucleic acid strand, complementary to the nucleic acid strand linked to the target-specific binding partner, wherein the following (i) or (ii) or both is met:

(i) the nucleic acid strand is linked to the target-specific binding partner with a first releasable linker; and
(ii) the HRP is linked to the complementary nucleic acid strand with a second releasable linker;

(4) optionally removing unbound enzyme linked to complementary nucleic acid strands;

(5) contacting the sample from step (3) or optionally step (4) with a substrate conjugate comprised of a detectably labeled phenol-including substrate, where the substrate and the detectable label are linked optionally with a third releasable linker;

(6) optionally removing unbound substrates;

(7) optionally imaging the sample to detect the detectable labels;

(8) optionally releasing the bound labels; and (9) optionally repeating steps (1)-(8) or any subset thereof and optionally if more than one target-specific binding partner is used, repeating steps (1)-(6) or any subset thereof prior to step (7) of imaging.

In some embodiments, after step (5), the phenol moiety is enzymatically converted into an activated state resulting in the deposition of the labels.

In some embodiments, the method may further comprise amplifying the nucleic acid strand (or a portion thereof) linked to the target-specific binding partner of step (1). In some embodiments, the amplifying step is performed prior to step (3).

In some embodiments, a method for testing a sample for the presence of one or more targets comprises:
(1) contacting a sample being tested for the presence of one or more targets with one or more target-specific binding partners, wherein each target-specific binding partner is linked to a nucleic acid strand and wherein target-specific binding partners of different specificity are linked to different nucleic acid strands;
(2) optionally removing unbound target-specific binding partners;
(3) contacting the sample from step (1) or optionally step (2) with an enzyme linked to a nucleic acid strand complementary to the nucleic acid strand linked to the target-specific binding partner;
(4) optionally removing unbound enzyme linked to complementary nucleic acid strands;
(5) contacting the sample from step (3) or optionally step (4) with a substrate conjugate comprised of a detectably labeled substrate, where the substrate and detectable label are linked optionally with a releasable linker;
(6) optionally removing unbound substrate conjugate;
(7) optionally deactivating the bound enzyme;
(8) optionally imaging the sample to detect the bound detectable labels; and
(9) optionally repeating steps (1)-(8) or any subset thereof and optionally if more than one target-specific binding partner is used, repeating steps (1)-(7) or any subset thereof prior to step (8) of imaging.

In some embodiments, the method may further comprise amplifying the nucleic acid strand (or a portion thereof) linked to the target-specific binding partner of step (1). In some embodiments, the amplifying step is performed prior to step (3).

In some embodiments, a method for testing a sample for the presence of one or more targets comprises:
(1) contacting a sample being tested for the presence of one or more targets with one or more target-specific binding partners, wherein each target-specific binding partner is linked to a nucleic acid strand and wherein target-specific binding partners of different specificity are linked to different nucleic acid strands;
(2) optionally removing unbound target-specific binding partners;
(3) contacting the sample from step (1) or optionally step (2) with a first member of a binding pair linked to a nucleic acid strand complementary to the nucleic acid strand linked to the target-specific binding partner,
(4) optionally removing unbound first member of binding pair linked to complementary nucleic acid strands;
(5) contacting the sample from step (3) or optionally step (4) with a second member of the binding pair linked to an enzyme and optionally removing unbound second member of the binding pair linked to the enzyme;
(6) contacting the sample from step (5) with a substrate conjugate comprised of a labeled substrate, where the substrate and label are linked optionally with a releasable linker;
(7) optionally removing unbound substrate conjugate;
(8) optionally deactivating the bound enzyme;
(9) optionally imaging the sample to detect the bound detectable labels; and
(10) optionally repeating steps (1)-(9) or any subset thereof and optionally if more than one target-specific binding partner is used, repeating steps (1)-(8) or any subset thereof prior to step (9) of imaging.

In some embodiments, the method further comprises (11) optionally releasing the bound detectable labels after step (9) by cleaving the releasable linker between the label and the substrate, and optionally repeating any of steps (1)-(9) and (11).

In some embodiments, the method may further comprise amplifying the nucleic acid strand (or a portion thereof) linked to the target-specific binding partner of step (1). In some embodiments, the amplifying step is performed prior to step (3).

In some embodiments, a method for testing a sample for the presence of one or more targets comprises:
(1) contacting a sample being tested for the presence of one or more targets with one or more target-specific binding partners, wherein each target-specific binding partner is linked to a nucleic acid strand and wherein target-specific binding partners of different specificity are linked to different nucleic acid strands;
(2) optionally removing unbound target-specific binding partners;
(3) contacting the sample from step (1) or optionally step (2) with an enzyme linked to a nucleic acid strand complementary to the nucleic acid strand linked to the target-specific binding partner
(4) optionally removing unbound enzyme linked to complementary nucleic acid strands;
(5) contacting the sample from step (3) or optionally step (4) with a substrate conjugate comprised of a nucleic acid strand-bound substrate, where the substrate and nucleic acid strand are linked optionally with a first releasable linker;
(6) optionally removing unbound substrate conjugates;
(7) optionally deactivating the bound enzymes;
(8) contacting the sample from step (5) or optionally steps (6)-(7) with a nucleic acid strand bound detectable label, linked optionally with a second releasable linker, where the nucleic acid strand is a specific binding pair member to the nucleic acid strand in step (5);
(9) optionally imaging the sample to detect the bound labels;
(10) optionally releasing the bound label from step (8); and
(11) optionally repeating steps (1)-(10) or any subset thereof and optionally if more than one target-specific binding partner is used, repeating steps (1)-(8) or any subset thereof prior to step (9) of imaging.

In some embodiments, the bound label is released with use of a releasable linker. In some embodiments, in step (10), the bound label is released by cleaving the releasable linker of step (5) or optionally step (8) or optionally steps (5) and (8). In some embodiments, the bound label is released without use of a releasable linker. In some embodiments, the bound label is released by dehybridization of the nucleic acid strands. In some embodiments the bound label is released by dehybridization of the nucleic acid strand from step (8) bound to the nucleic acid strand from step (5).

In some embodiments, the method may further comprise amplifying the nucleic acid strand (or a portion thereof) linked to the target-specific binding partner of step (1). In some embodiments, the amplifying step is performed prior to step (3).

In some embodiments, the method may further comprise amplifying the nucleic acid strand (or a portion thereof) of the nucleic acid strand-bound substrate of step (5). In some embodiments, the amplifying step is performed after step (5) or optional step (6) or optional step (7).

In some embodiments, the method may further comprise first amplifying the nucleic acid strand (or a portion thereof) linked to the target-specific binding partner of step (1) and second amplifying the nucleic acid strand of the nucleic acid strand-bound substrate of step (5). In some embodiments, the first amplifying step is performed prior to step (3); and the second amplifying step is performed after step (5) or optional step (6) or optional step (7).

In some embodiments, a method for testing a sample for the presence of one or more targets comprises:
(1) contacting a sample being tested for the presence of one or more targets with one target-specific binding partner, wherein the target-specific binding partner is linked to a nucleic acid strand;
(2) optionally removing unbound target-specific binding partners,
(3) contacting the sample with an HRP-bound nucleic acid strand, complementary to the nucleic acid strand linked to the target-specific binding partner;
(4) optionally removing unbound enzyme linked to complementary nucleic acid strands;
(5) contacting the sample from step (3) or optionally step (4) with a substrate conjugate comprised of a detectably labeled phenol-including substrate, where the substrate and the detectable label are linked optionally with a releasable linker;
(6) optionally removing unbound substrate;
(7) optionally deactivating the HRP;
(8) optionally imaging the sample to detect the bound detectable labels; and
(9) optionally repeating steps (1)-(8) or any subset thereof and optionally if more than one target-specific binding partner is used, repeating steps (1)-(7) or a subset thereof prior to step (8).

In some embodiments, the method may further comprise amplifying the nucleic acid strand (or a portion thereof) linked to the target-specific binding partner of (1). In some embodiments, the amplifying step is performed prior to step (3).

In some embodiments, the enzyme is deactivated using an enzyme deactivator, wherein the enzyme deactivator comprises dithiothreitol (DTT), tris(2-carboxyethyl)phosphine (TCEP), a reduced glutathione, a peroxide, a cyanide, a fluoride, or an azide.

In some embodiments, step (7) of deactivating the bound enzyme is performed for less than 20 minutes, less than 10 minutes, less than 5 minutes, less than 2 minutes, or less than or equal to 1 minute. In some embodiments, step (7) of deactivating the bound enzyme is performed for less than 20 minutes. In some embodiments, step (7) of deactivating the bound enzyme is performed for less than 10 minutes. In some embodiments, step (7) of deactivating the bound enzyme is performed for less than 5 minutes. In some embodiments, step (7) of deactivating the bound enzyme is performed for less than 2 minutes. In some embodiments, step (7) of deactivating the bound enzyme is performed for less than or equal to 1 minute.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A provides a schematic that does not involve stacking. FIG. 1B provides a schematic that does involve stacking.

FIG. 4A shows an exemplary embodiment in which the enzyme is cleaved.

FIG. 4B shows an exemplary embodiment in which the enzyme is deactivated.

DESCRIPTION OF THE EMBODIMENTS

I. Definitions

Figure 1A:
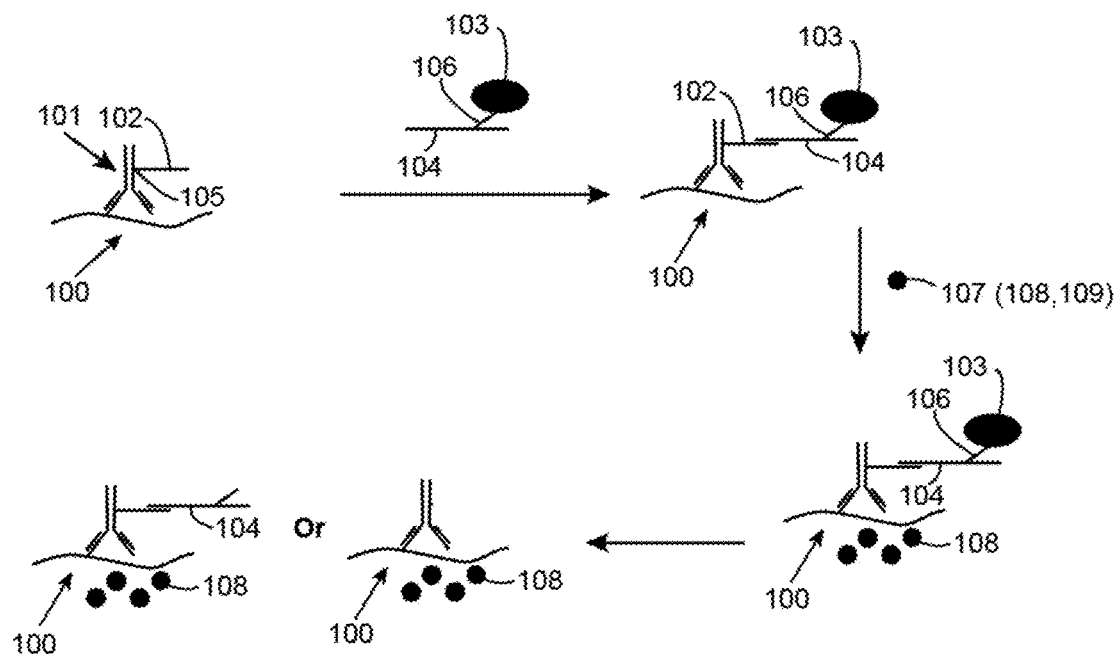
FIGS. 1A-B provides two schematics for multiplexed catalyzed reporter deposition (CARD).

The term "deposition" means directed binding of an activated substrate conjugate to the receptor which results from the formation of a specific binding pair interaction as described below.

The term "receptor" means a site which will bind to the activated substrate conjugate through the formation of a specific binding pair interaction as described below.

The term "activated substrate conjugate" means that the substrate conjugate has been primed by the reporter enzyme to bind with the receptor.

The term "detectably labeled" substrate conjugate means that the substrate can be coupled to either a detectable label (the term "reporter" may be used interchangeably) or to an unlabeled first member of a specific binding pair to facilitate detection following deposition. When the substrate is coupled to an unlabeled member of a specific binding pair, following deposition, the substrate-specific binding pair complex is reacted with the second member of the binding pair which is coupled to a reporter (or a label). Alternately, the substrate-specific binding pair complex can be pre-reacted with the detectably labeled second member of the specific binding pair prior to deposition.

As described herein, the term "amplifying" or "amplification" refers to increasing the number of copies of a nucleic acid sequence, such as a nucleic acid strand or portion thereof (such as a barcode).such that multiple copies of the nucleic acid sequence are linked to a respective target-specific binding partner. Various amplification methods known in the art to increase the number of copies of a nucleic acid sequence may be used. Examples of nucleic acid amplification methods include hybridization chain reaction (HCR) (Dirks et al., 2014, PMID: 15492210, 24712299), DNA hairpin-based dendrimerization reaction (HDR) (Yin et al., 2008, PMID 18202654), rolling circle amplification (RCA), primer exchange reaction (PER), and other nucleic acid amplification method, for example, s as described in WO 2018/107054; WO 2017/143006; WO 2018/132392A2, the contents of each of which are herein incorporated by reference. This amplification is distinct from signal amplification resulting from CARD.

II. Methods of Multiplexed Catalyzed Reporter Deposition

The present application discloses a method for multiplex catalyzed reporter deposition (CARD). Schematics for multiplexed catalyzed reporter deposition are provided in FIGS. 1A, 1B, 2, and 3.

In accordance with the description, in some embodiments, a method to test a sample for the presence of one or more targets comprises:

(1) contacting a sample being tested for the presence of one or more targets with one or more target-specific binding partners, wherein each target-specific binding partner is linked to a nucleic acid strand optionally using a releasable linker and wherein target-specific binding partners of different specificity are linked to different nucleic acid strands, (2) optionally removing unbound target-specific binding partners, (3) contacting the sample with an enzyme or a member of a specific binding pair for subsequent enzyme labeling, linked to a nucleic acid strand complementary to the strand on the target-specific binding partner, wherein if the nucleic acid strand bound to the target-specific binding partner is not linked using a releasable linker, then the enzyme or member of a specific binding pair is linked to the complementary strand of step (3) using a releasable linker, and if the nucleic acid strand bound to the target-specific binding partner is linked using a releasable linker, then the enzyme or member of a specific binding pair is linked to the complementary strand of step (3) optionally using a releasable linker, (4) optionally removing unbound enzyme or specific binding pair member linked to complementary nucleic acid strands, (5) if a member of a specific binding pair is utilized in step (3) the sample is contacted with the second member of the specific binding pair linked to an enzyme optionally with a releasable linker, and optionally removing unbound enzyme linked second member of the specific binding pair, (6) contacting the sample with a substrate conjugate comprised of a detectably labeled substrate, where the substrate and label are linked optionally with a releasable linker, (7) optionally removing unbound substrate conjugate, (8) optionally releasing the bound enzyme, first or second specific binding pair members, (9) optionally detecting the bound detectable labels,

(10) optionally repeating steps (1)-(9) or any subset thereof and optionally if more than one target-specific binding partner is used, repeating steps (1)-(8) or any subset thereof prior to step (9) of detecting.

In some embodiments, the method may further comprise amplifying the nucleic acid strand (or a portion thereof) linked to the target-specific binding partner of step (1). In some embodiments, the amplifying step is performed prior to step (3).

A. Multiplex CARD with Enzyme Bound to Probe Strand

In some embodiments, a method for testing a sample for the presence of one or more targets comprises:

(1) contacting a sample being tested for the presence of one or more targets with one or more target-specific binding partners, wherein each target-specific binding partner is linked to a nucleic acid strand and wherein target-specific binding partners of different specificity are linked to different nucleic acid strands;

(2) optionally removing unbound target-specific binding partners;

(3) contacting the sample from step (1) or optionally step (2) with an enzyme linked to a nucleic acid strand complementary to the nucleic acid strand linked to the target-specific binding partner, wherein the following (i) or (ii) or both is met:
  (i) the nucleic acid strand is linked to the target-specific binding partner with a first releasable linker; and
  (ii) the enzyme is linked to the complementary nucleic acid strand with a second releasable linker;

(4) optionally removing unbound enzyme linked to complementary nucleic acid strands;

(5) contacting the sample from step (3) or optionally step (4) with a substrate conjugate comprised of a detectably labeled substrate, where the substrate and a label are linked optionally with a third releasable linker;

(6) optionally removing unbound substrate conjugate;

(7) optionally releasing the bound enzyme;

(8) optionally imaging the sample to detect the bound detectable labels; and (9) optionally repeating steps (1)-(8) or any subset thereof and optionally if more than one target-specific binding partner is used, repeating steps (1)-(7) or any subset thereof prior to step (8) of imaging.

In some embodiments, in step (5), the substrate conjugate comprised of the detectably labeled substrate reacts with the enzyme to form an activated substrate conjugate, and the activated substrate conjugate binds to a receptor for the activated substrate conjugate.

In some embodiments, the method may further comprise amplifying the nucleic acid strand (or a portion thereof) linked to the target-specific binding partner of step (1). In some embodiments, the amplifying step is performed prior to step (3).

In some embodiments, the receptor for the activated substrate conjugate is present in the sample, resulting in the deposition of the detectable labels.

In some embodiments, all the labels are removed and the above steps for labeling start again ("stacking") to enable another round of multiplexing. In some embodiments, the method further comprises (10) releasing the bound detectable labels after the imaging step (8) and optionally repeating steps (1)-(10) or any subset thereof. In some embodiments, the bound labels are released with use of a releasable linker. In some embodiments, in step (10), the bound label is released by cleaving the third releasable linker. In some embodiments, the bound labels are released without a use of releasable linker FIGS. 1A-1B show embodiments for the method of multiplexed CARD that does not involve stacking (FIG. 1A) and involves stacking (FIG. 1B).

In the multiplexed CARD without stacking as shown in FIG. 1A, first, a sample (tissue, 100) bound to a target-specific binding partner (antibody, 101) where the target-specific binding partner is linked to a nucleic acid strand comprising a barcode (barcode, 102) is provided and contacted with an enzyme (103) linked to a nucleic acid strand (probe, 104) complementary to the nucleic acid strand comprising a barcode (barcode, 102) linked to the antibody (101). The nucleic acid strand comprising a barcode (barcode, 102) is linked to the antibody (101) with a first releasable linker (105). Alternatively, the enzyme (103) is linked to the complementary nucleic acid strand, which comprises a sequence complementary to the barcode(probe, 104) with a second releasable linker (106). Optionally, unbound enzyme linked to complementary nucleic acid strands are removed.

Next, the sample (100) is contacted with a substrate conjugate (labeled substrate, 107) containing a detectable label (108). The detectable label reacts with the enzyme to form an activated substrate conjugate, and the activated substrate conjugate binds to a receptor for the activated substrate conjugate present in a sample, resulting in the deposition of the detectable labels on the sample (108). Unbound substrate conjugates (107) are optionally removed by a washing step. The enzyme then is released by cleaving a releasable linker with a cleaving agent. Depending on use of the first releasable linker (105) or the second releasable linker (106), after the cleavage of the releasable linker, (bottom left) the enzyme (103) linked to the complementary nucleic acid strand (probe, 104) is removed or (bottom right), the nucleic acid strand is cleaved such that the enzyme, the nucleic acid strand comprising a barcode (barcode, 102) linked to the antibody (101) and the complementary nucleic acid strand (probe, 104) linked to the enzyme are removed. The above-deposition of detectable labels can be repeated for each target. Then, the sample is imaged to detect bound detectable labels of different targets.

Figure 1B:
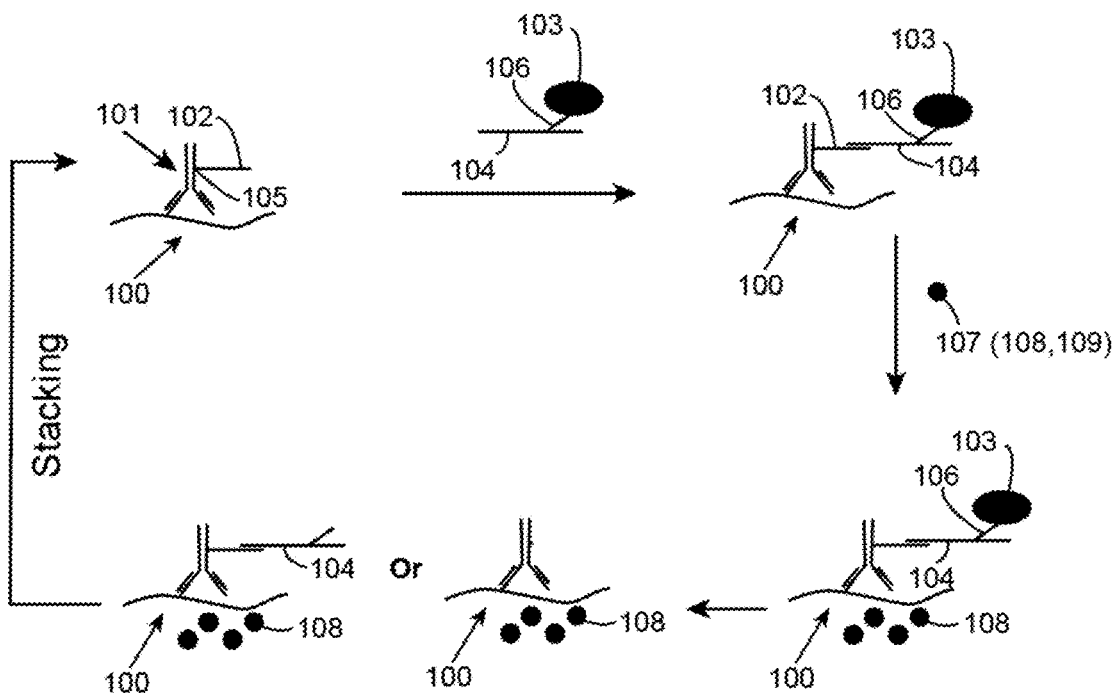

In the multiplexed CARD with stacking as shown in FIG. 1B, the substrate (107) and the label (108) can be linked with a third releasable linker (109); and after the imaging step, all of the bound labels are removed by cleaving the third releasable linker (109), and the above described steps are repeated for deposition of labels for detection of more targets ("stacking").

Figure 3:
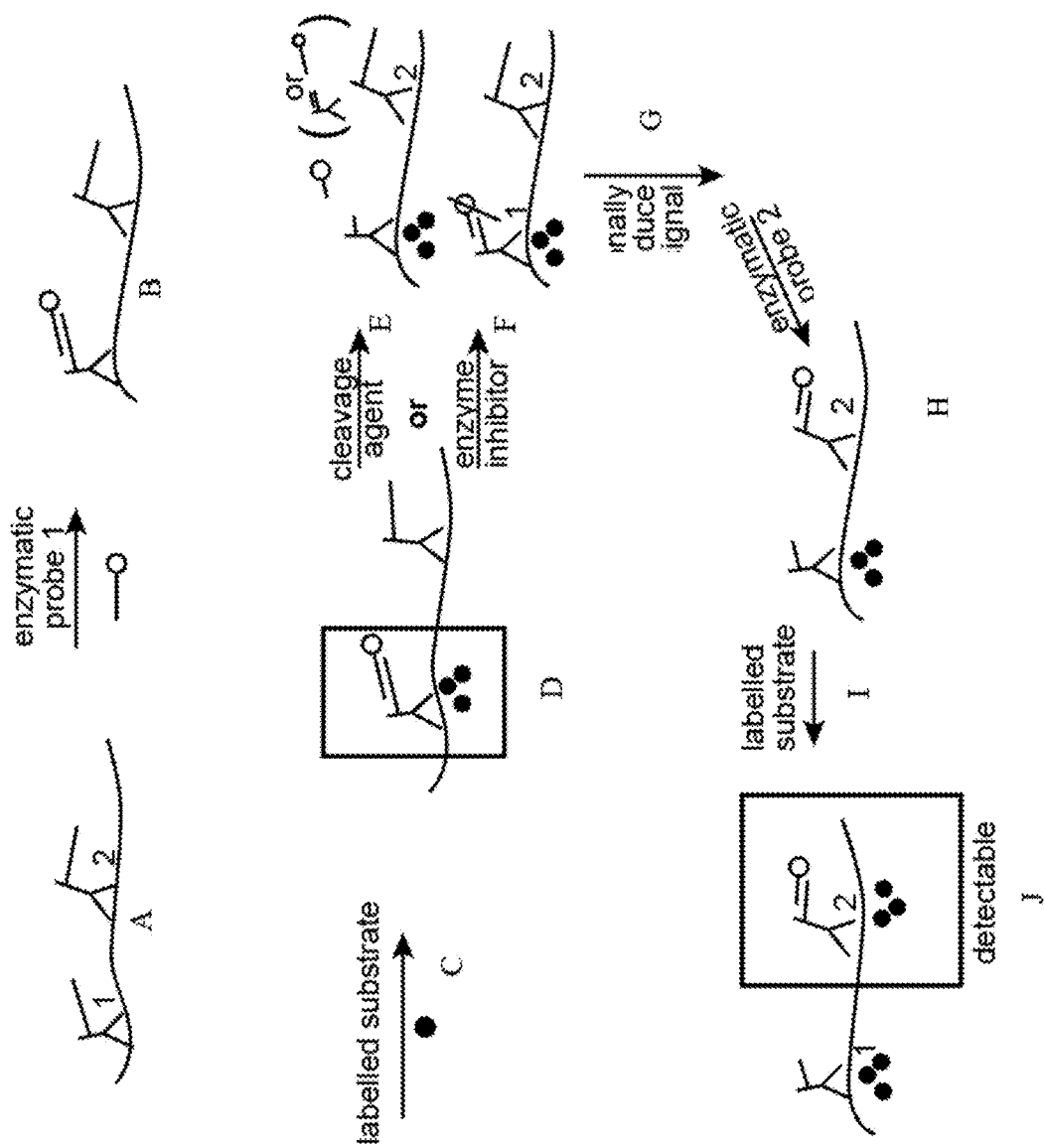
FIG. 3 shows an exemplary embodiment in which two target molecules are detected using a multiplex method described herein.

FIG. 3 also shows an exemplary embodiment in which two target molecules are detected using the method described herein. In a tissue sample, two targets 1 and 2 are bound to respective antibodies, each antibody linked to a distinct nucleic acid strand (Step A). An enzyme linked to a nucleic acid strand (enzymatic probe 1) where the nucleic acid strand is complementary to the nucleic acid strand linked to the antibody for target 1 is bound to the nucleic acid strand linked to the antibody for target 1 and unbound enzymatic probes are optionally washed (Step B). Next, a labeled substrate is added to the sample (Step C), and reacts with the enzyme to form an activated substrate conjugate. The activated substrate conjugate binds to a receptor for the activated substrate conjugate present in the sample, resulting in the deposition of the detectable labels (Step D). The enzymatic probes 1 are released by cleaving a releasable linker with a cleaving agent (Step E) or deactivating the enzyme by enzyme inhibitor (or enzyme deactivator) (Step F). In Step 3, depending on the location of the releasable linker, the enzyme is removed or the barcode and the probe linked to the enzyme are also removed with the enzyme (Step G). The above-deposition of labels can be repeated for target 2 (Steps H and I). Then, the sample is imaged to detect bound detectable labels of both targets. Optionally, the signals from the labels may be reduced as necessary by using methods well known in the art (e.g., chemical bleaching, photo-bleaching, and/or photochemical bleaching).

B. Multiplex CARD with Binding Pairs

In some embodiments, a method for testing a sample for the presence of one or more targets comprises:

(1) contacting a sample being tested for the presence of one or more targets with one or more target-specific binding partners, wherein each target-specific binding partner is linked to a nucleic acid strand and wherein target-specific binding partners of different specificity are linked to different nucleic acid strands;

(2) optionally removing unbound target-specific binding partners;

(3) contacting the sample from step (1) or optionally step (2) with a first member of a binding pair linked to a nucleic acid strand complementary to the nucleic acid strand linked to the target-specific binding partner, wherein the following (i) or (ii) or both is met:
  (i) the nucleic acid strand is linked to the target-specific binding partner with a first releasable linker; and
  (ii) the first member of the binding pair is linked to the complementary nucleic acid strand with a second releasable linker;

(4) optionally removing unbound first member of binding pair linked to complementary nucleic acid strands;

(5) contacting the sample from step (3) or optionally step (4) with a second member of the binding pair linked to an enzyme optionally with a third releasable linker, and optionally removing unbound second member of the binding pair linked to the enzyme;

(6) contacting the sample from step (5) with a substrate conjugate comprised of a labeled substrate, where the substrate and label are linked optionally with a fourth releasable linker;

(7) optionally removing unbound substrate conjugate;

(8) optionally releasing the bound first or second member of the binding pair;

(9) optionally imaging the sample to detect the bound detectable labels; and

(10) optionally repeating steps (1)-(9) or any subset thereof and optionally if more than one target-specific binding partner is used, repeating steps (1)-(8) or any subset thereof prior to step (9) of imaging.

In some embodiments, the method may further comprise amplifying the nucleic acid strand linked to the target-specific binding partner of step (1). In some embodiments, the amplifying step is performed prior to step (3).

In some embodiments, for the stacking, the method further comprises, (11) optionally releasing the bound detectable labels. In some embodiments, the bound labels are released by releasing the third releasable linker between the label and the substrate. In some embodiments, the bound labels are released without a use of releasable linker In some embodiments, the method further comprises (11) optionally releasing the bound detectable labels after the imaging step (9) by releasing the third releasable linker and further comprising optionally repeating steps (1)-(11) or any subset thereof. In some embodiments, a method for testing a sample for the presence of one or more targets comprises:

(1) contacting a sample being tested for the presence of one or more targets with one or more target-specific binding partners, wherein each target-specific binding partner is linked to a nucleic acid strand and wherein target-specific binding partners of different specificity are linked to different nucleic acid strands;

(2) optionally removing unbound target-specific binding partners;

(3) contacting the sample from step (1) or optionally step (2) with an enzyme linked to a nucleic acid strand complementary to the nucleic acid strand linked to the target-specific binding partner, wherein the following (i) or (ii) or both is met:
  (i) the nucleic acid strand is linked to the target-specific binding partner with a first releasable linker; and
  (ii) the enzyme is linked to the complementary nucleic acid strand with a second releasable linker;

(4) optionally removing unbound enzyme linked to complementary nucleic acid strands;

(5) contacting the sample from step (3) or optionally step (4) with a substrate conjugate comprised of a nucleic acid strand-bound substrate, where the substrate and nucleic acid strand are linked optionally with a third releasable linker;

(6) optionally removing unbound substrate conjugate;

(7) optionally releasing the bound enzyme;

(8) contacting the sample from step (5) or optionally steps (6)-(7) with a nucleic acid strand-bound detectable label, linked optionally with a fourth releasable linker, where the nucleic acid strand is a specific binding pair member to the nucleic acid strand in step (5);

(9) optionally imaging the sample to detect the bound labels;

(10) optionally releasing the bound label from step (8); and

(11) optionally repeating steps (1)-(10) or any subset thereof and optionally if more than one target-specific binding partner is used, repeating steps (1)-(8) or any subset thereof prior to step (9) of imaging.

In some embodiments, the bound label is released with a releasable linker. In some embodiments, the bound label is released by cleaving the releasable linker of step (5) or optionally step (8) or optionally steps (5) and (8). In some embodiments, the bound label is released without use of a releasable linker. In some embodiments, the bound labels are released by dehybridization of the nucleic acid strands bound to each other. In some embodiments, the bound labels are released by dehybridzation of the nucleic acid strand in step (8) bound to the nucleic acid strand in step (5). Dehybridzation of the nucleic acid may be achieved conventional methods known in the art, including heat, addition of chaotropic agents (e.g., urea, formamide, and guanidinium chloride), and low ionic strength. Increasing the temperature or lowering the ionic strength of the medium containing the nucleic acid strands disrupts the binding affinities between the nucleic acid strands. Heat, one or more chaotropic agents, and low ionic strength can each be used independently to dehybridize nucleic acids; or a combination of one or more of these conditions can be used. As used herein, "low ionic strength" means the ionic strength of the medium measured by the amount of salt concentration in the medium being less than 300 mM. In an embodiment, the salt concentration is below the concentration required for the Tm to be lower than the ambient temperature, e.g., lower than 70 mM. The hybridization rate decreases with lower salt concentration. Dehybridization at low ionic strength may be achieved by conventional methods, for example, reducing the salt (e.g., Nat) concentration by adding water.

In some embodiments, the method may further comprise amplifying the nucleic acid strand (or a portion thereof) linked to the target-specific binding partner of step (1). In some embodiments, the amplifying step is performed prior to step (3).

In some embodiments, the method may further comprise amplifying the nucleic acid strand (or a portion thereof) of the nucleic acid strand-bound substrate of step (5). In some embodiments, the amplifying step is performed after step (5) or optional step (6) or optional step (7).

In some embodiments, the method may further comprise first amplifying the nucleic acid strand (or a portion thereof) linked to the target-specific binding partner of step (1) and second amplifying the nucleic acid strand of the nucleic acid strand-bound substrate of step (5). In some embodiments, the first amplifying step is performed prior to step (3); and the second amplifying step is performed after step (5) or optional step (6) or optional step (7).

Figure 2:
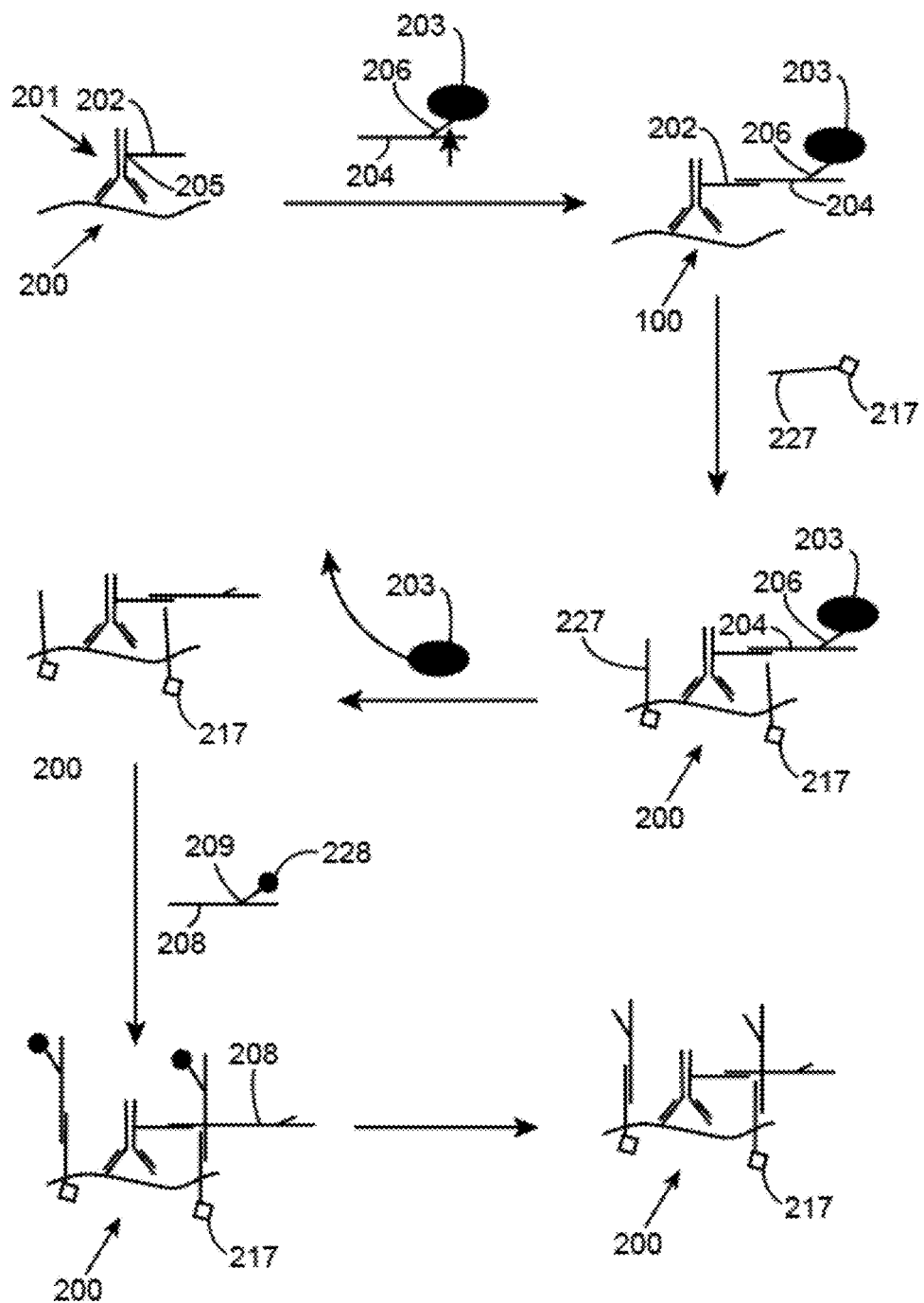
FIG. 2 provides a schematic for multiplexed catalyzed reporter deposition (CARD) using a binding pair, where the binding pair is a nucleic acid strand (which is or comprises a barcode) and a complementary nucleic acid strand.

FIG. 2 shows an embodiment of the method of multiplexed catalyzed reporter deposition (CARD) using a binding pair, where the binding pair is a nucleic acid strand (which is or comprises a barcode) and a complementary nucleic acid strand.

First, a sample (tissue, 200) bound to a target-specific binding partner (antibody, 201) where the target-specific binding partner is linked to a nucleic acid strand comprising a barcode (barcode, 202) is provided and contacted with an enzyme (203) linked to a nucleic acid strand (probe, 204) complementary to the nucleic acid strand (barcode, 202) linked to the antibody (201). The nucleic acid strand (barcode, 202) is linked to the antibody (201) with a first releasable linker (205). Alternatively, the enzyme (203) is linked to the complementary nucleic acid strand (probe, 204) with a second releasable linker (206). Optionally, unbound enzyme (203) linked to complementary nucleic acid strands (202) are removed.

Next, the sample (200) is contacted with a nucleic acid strand-bound substrate (217), where the substrate (217) and nucleic acid strand (227) deposit on the tissue. Then, unbound substrate conjugate and/or the bound enzyme are removed by cleaving a releasable linker with a cleaving agent (e.g., TCEP, DTT or periodate). The above-deposition of nucleic acid bound-substrates can be repeated for each target. The washing step is optional for the last round of deposition.

Next, the tissue sample (200) is contacted with a nucleic acid strand-bound detectable label (208), linked optionally with a fourth releasable linker (209), where the nucleic acid strand (probe, 208) is a specific binding pair member to the nucleic acid strand complementary to probe(227). If four primary antibodies are provided to bind to four different targets, four different labeled probes (208) are provided. The tissue sample (200) is imaged to detect detectable labels bound to different targets. To detect additional targets, after the imaging step, all of the bound labels are removed by a washing step to cleave a third releasable linker (209) between the label and the probe (208) using a cleaving agent, and the above described steps are repeated for deposition of labels for detection of more targets ("stacking"). The above described steps or any subset thereof are repeated as needed for detection of more targets.

C. Embodiments Using Phenolic Substrate

In some embodiments, the multiplexed CARD method is a tyramide signal amplification (TSA) method that has been multiplexed. One may also use the TSA amplification method where the fluorophore can be readily bleached. For example, many cyanine fluorophores and Alexa fluorophore can be readily bleached by hydrogen peroxide in acidic or basic conditions (PMID: 26399630). Alternatively, one can synthesize a TSA dye that contains a cleavable bond between the tyramide and the fluorophore. In this case the fluorophore can be deactivated by cleaving this bond and washing.

In some embodiments, a method for testing a sample for the presence of one or more targets comprises (1) contacting a sample being tested for the presence of one or more targets with one target-specific binding partner, wherein the target-specific binding partner is linked to a nucleic acid strand, (2) optionally removing unbound target-specific binding partners, (3) contacting the sample with an HRP-bound nucleic acid strand, complementary to the nucleic acid strand linked to the target-specific binding partner, wherein the following (i) or (ii) or both is met: (i) the nucleic acid strand is linked to the target-specific binding partner with a first releasable linker; and (ii) the HRP is linked to the complementary nucleic acid strand with a second releasable linker; (4) optionally removing unbound enzyme linked to complementary nucleic acid strands; (5) contacting the sample from step (3) or optionally step (4) with a substrate conjugate comprised of a detectably labeled phenolic substrate, where the substrate and the detectable label are linked optionally with a third releasable linker; (6) optionally removing unbound substrate; (7) optionally imaging the sample to detect the sample; (8) optionally releasing the bound labels; and (9) optionally repeating steps (1)-(8) or any subset thereof and optionally if more than one target-specific binding partner is used, repeating steps (1)-(6) or any subset thereof prior to step (7) of imaging.

In some embodiments, after step (5), the phenolic substrate is enzymatically converted into an activated state resulting in the deposition of the labels. In some embodiments, the phenolic substrate is tyramide.

In some embodiments, the method may further comprise amplifying the nucleic acid strand (or a portion thereof) linked to the target-specific binding partner. In some embodiments, the amplifying step is performed prior to step (3) of contacting the sample with an HRP-bound nucleic acid strand, complementary to the nucleic acid strand linked to the target-specific binding partner. Catalyzed reporter deposition is a method of signal amplification and utilizes an enzyme, coupled directly or indirectly to a target-specific binding partner, which catalyzes the conversion of a substrate conjugate, comprised of a detectably labeled substrate, to an activated substrate conjugate which binds to a receptor for the activated substrate conjugate, resulting in the deposition of detectable labels. Examples of previous catalyzed reporter deposition were described, for example, in U.S. Pat. Nos. 5,196,306, 5,583,001 and 5,731,158.

Catalyzed reporter deposition has been utilized to enhance signals in immunohistochemistry, immunocytochemistry, in situ hybridization, ELISA, flow cytometry, electron microscopy, and other applications.

There are several limitations in prior catalyzed reporter deposition, however. One of the limitations is the ability to multiplex, i.e., detect multiple assay targets in the same assay. The limitation is exacerbated when utilizing antibodies from the same species in an assay. Detection of two targets utilizing antibodies of the same species has been accomplished by using catalyzed reporter deposition to detect one target, and standard detection for a second target (Shindler J. Histochem Cytochem 1996 Vol 44 No 11 1331-1335).

In previous attempts for multiplexing immunohistochemistry assays using catalyzed reporter deposition, microwaving the tissue sections was performed in between each round of reporter deposition (Toth J. Histochem Cytochem 2007 Vol 55 (6) 545-554). Microwaving removes the antibodies and reporter enzyme while the detectable labels remain intact. Microwaving adds many steps as each antibody and reporter needs to be added sequentially, followed by microwaving to remove them. As an example of using microwaving, the Opal™ 7 Solid Tumor Immunology Kit (PerkinElmer) requires over 90 minutes per cycle, and the entire procedure takes two days to complete. Microwaving can also alter or damage a sample being imaged.

In another previous attempt, heat deactivation was employed to detect a 5-plex assay (Zhang, W., Hubbard, A., Jones, T. et al j immunotherapy cancer (2015) 3(Suppl 2): P111). The four heat deactivation cycles resulted in reduction of fluorescence of 12-50% of the five fluorescent labels used. The assay took nine hours to complete. Other variations of heating have been described in U.S. Pat. Nos. 9,689,875 and 9,874,571, incorporated herein by reference for the teachings of heating variations. Heat deactivation may, however, alter or damage a sample being imaged.

With microwaving or heat deactivation between cycles, the number of detectable targets is still limited by the number of labels a reader and software can distinguish. In the field of immuno-oncology, the number of targets desired to be detected is already in the 12 to 20 range, and this is well beyond the limits of readers and software.

The above-described methods according to the present disclosure provide a signal amplification method that can be multiplexed in a simpler and faster way, avoiding harsh sample treatment such as heat and microwaving, as well as have the capability of multiplexing at higher levels.

D. Kits

In some embodiments, a kit includes a composition including (1) one or more target-specific binding partners, each binding partner bound to a nucleic acid strand, (2) an enzyme linked to a nucleic acid strand complementary to the nucleic acid strand bound to the one or more target-specific binding partners, wherein the following (i) or (ii) or both is met: (i) the nucleic acid strand is linked to each target-specific binding partner with a first releasable linker; and (ii) the enzyme is linked to the complementary nucleic acid strand with a second releasable linker; and (3) a substrate conjugate comprised of a detectably labeled substrate, where the substrate and label are linked optionally with a third releasable linker In some embodiments a kit includes a composition including composition comprising (1) one or more target-specific binding partners, each binding partner bound to a nucleic acid strand, (2) a binding pair comprising: a first member linked to a nucleic acid strand complementary to the nucleic acid strand bound to each target-specific binding partner, and a second member linked to an enzyme, wherein the following (i) or (ii) or both is met: (i) the nucleic acid strand is linked to each target-specific binding partner with a first releasable linker; and (ii) the first member of the binding pair is linked to the complementary nucleic acid strand with a second releasable linker; and (3) a substrate conjugate comprised of a detectably labeled substrate, where the substrate and label are linked optionally with a third releasable linker, wherein the second member of the binding pair is linked to an enzyme with a fourth releasable linker In some embodiments, a kit further includes a fluidic system to perform fluid exchange steps, a software to control the fluidic system and time and/or synchronize the fluidic steps with the imaging steps. In some embodiments, a kit further includes an imaging chamber to affix on the sample of interest with at least one optically transparent side to allow imaging of the sample.

III. Components of the Method

A. Enzymes for Use in CARD

Enzymes suitable for being coupled directly or indirectly to a target-specific binding partner include hydrolases, lyases, oxidoreductases, transferases isomerases, ligases, peroxidases, oxidases, phosphatases, esterases and glycosidases. Specific examples include alkaline phosphatase, lipases, beta-galactosidase and horseradish peroxidase (HRP). More than one enzyme can be used simultaneously in conjunction with unique substrate conjugate for each enzyme if desired.

B. Specific Binding Pairs

Members of specific binding pairs suitable for use in practicing the invention can be of the immune or nonimmune type. Immune specific binding pairs are exemplified by antigen/antibody systems or hapten/antihapten systems. The antibody member, whether polyclonal, monoclonal or an immunoreactive fragment thereof, of the binding pair can be produced by customary methods familiar to those skilled in the art. The terms immunoreactive antibody fragment or immunoreactive fragment mean fragments which contain the binding region of the antibody. Such fragments may be Fab-type fragments which are defined as fragments devoid of the Fc portion, e.g., Fab, Fab' and F(ab')$_2$ fragments, obtained by reductive cleavage of the disulfide bonds connecting the heavy chain components of the intact antibody. Fragments may also be single domain antibodies, derived from heavy chains or light chains antibodies, and may include nanobodies. If the antigen member of the specific binding pair is not immunogenic, e.g., a hapten, it can be covalently coupled to a carrier protein to render it immunogenic.

Non-immune binding pairs include systems wherein the two components share a natural affinity for each other but are not antibodies. Exemplary non-immune binding pairs are biotin-avidin or biotin-streptavidin, complementary probe nucleic acids folic acid-folate binding protein, etc. Also included are non-immune binding pairs which form a covalent bond with each other. Exemplary covalent binding pairs include sulfhydryl reactive groups such as maleimides and haloacetyl derivatives and amine reactive groups such as isothiocyanates, succinimidyl esters, sulfonyl halides and click chemistry and coupler dyes such as 3-methyl-2-benzothiazolinone hydrazone (MBTH) and 3-(dimethyl-amino) benzoic acid (DMAB), etc.

Complementary probe nucleic acids can be used to increase the signal by increasing the number of binding sites for nucleic acid probes using methods such as Rolling Circle Amplification (Paul M Lizardi, et al. Nature Genetics, 19(3):225-232, 1998) and Primer Exchange Reaction (WO 2017/143006 A1).

C. Target Specific Binding-Partners

Target specific binding-partners suitable for practicing the invention can be of the immune or nonimmune type. Immune specific binding pairs are exemplified by antigen/antibody systems. The antibody member, whether polyclonal, monoclonal or an immunoreactive fragment thereof, of the binding pair can be produced by customary methods familiar to those skilled in the art. The terms immunoreactive antibody fragment or immunoreactive fragment mean fragments which contain the binding region of the antibody. Such fragments may be Fab-type fragments which are defined as fragments devoid of the Fc portion, e.g., Fab, Fab' and F(ab')2 fragments, obtained by reductive cleavage of the disulfide bonds connecting the heavy chain components of the intact antibody. Fragments may also be single domain antibodies, derived from heavy chains or light chains antibodies, and may include nanobodies. If the antigen member of the specific binding pair is not immunogenic, e.g., a carbohydrate or phosphorylated amino acid, it can be covalently coupled to a carrier protein to render it immunogenic.

Table 1 provides a representative listing of targets and corresponding target recognition moieties.

TABLE 1

Representative Targets and Target Recognition Moieties

| Target | Target Recognition Moiety | Source or Sequence |
|---|---|---|
| Any protein | Antibody (Class A) | Variable |
| Fluorescein (chemical compound) | Antibody (Class A) | Abcam, product # ab7253 |
| Digoxigenin (chemical compound) | Antibody (Class A) | Abcam, product # ab76907 |
| Biotin | Avidin/Streptavidin (Class B) | |
| Epidermal growth factor receptor (EGFR, protein) | Epidermal growth factor (EGF, Class B) | |
| Platelet-derived growth factor receptor (PDGFR, protein) | Platelet-derived growth factor (PDGF, Class B) | |
| Epidermal growth factor receptor (EGFR, protein) | E07 aptamer (Class C) | Li et al., PloS ONE, 2011; 6(6): e20299 |
| Integrins (protein) | RGD-containing peptides (Class B) | |
| TNF-α(protein) | T09.12 peptide (Class C) | Xu et al., Chem Biol. 2002 August; 9(8): 933-42. |
| HaloTag (enzyme) | Halogenated compounds (Class D) | Bioconjug Chem. 2015 Jun. 17; 26(6): 975-86. |
| Oxidosqualene cyclase (OSC, enzyme) | [3H]29-methylidene-2,3-oxidosqualene ([3H]29-MOS, Class D) | Biochem Biophys Res Commun. 1992 Aug. 31; 187(1): 32-8. |

Table 2 provides a listing of additional targets. Antibodies and other known binding partners of these targets may be used as target recognizing moieties.

TABLE 2

Additional Representative Targets

Actin
AIF
AKT
alpha-synuclein
amyloid precursor protein
annexin
arrestin
BAD
BAX
Bcl-2
Bcl-2
beta-catenin
BRCA1
cAMP
caveolin
CD20
CD3
CD4
CD45
CD68
CD8
collagen
CREB
DNA
E-Cadherin
EGFR TABLE 2-continued Additional Representative Targets EpCAM
ER
ERK
ERK
FOXA
FOXP3
GABA
GAPDH
GFP
granzymeB
GRB2
HER2
HER3
HIF-1
histoneH3
HSP27
HSP70
HSP90
keratin
Ki67
lamin
MAPK
MEK
MET
MMP
mTOR
MYC
NeuN
p21
p53
PAX
PD-1
PD-L1
PI3K
PR
PSD95
RAS
SOX
STAT
synapsin
Tau
TOM20
tubulin
ubiquitin
VEGF
vimentin
WNT Non-immune binding pairs include systems wherein the two components share a natural affinity for each other but are not antibodies.

Exemplary non-immune binding pairs include complementary probe nucleic acids and aptamers. Complementary probe nucleic acids are suitable target specific binding partners for nucleic acid (e.g., DNA or RNA) targets.

1. Nucleic Acid Strand Used in the Binding Pair

In some embodiments, the nucleic acids used in the binding pair are single stranded nucleic acids such as single stranded DNA, RNA, or a nucleic acid analog. A nucleic acid analog (also known as non-natural nucleic acid) may include an altered phosphate backbone, an altered pentose sugar, and/or altered nucleobases. Nucleic acid analogs may include, but are not limited to, 2'-O-Methyl ribonucleic acid, 2'-fluoro ribonucleic acid, peptide nucleic acid, morpholino and locked nucleic acid, glycol nucleic acid, and threose nucleic acid.

In some embodiments, the nucleic acid strand comprises single-stranded nucleic acids and may be from about 5 to 20 nucleotides long, from about 8 to 15, or from about 10 to 12 nucleotides long. In some embodiments, the nucleic acid strand is about 5, 8, 9, 10, 11, 12, 13, 14, 15, 18, or 20 nucleotides long.

The nucleic acid strand may be an independent element or it may be part of the target recognizing moiety.

The nucleic acid strand may be provided in a liquid medium or buffer solution.

The target-specific binding partner may be provided in a liquid medium or buffer solution.

D. Binding of an Activated Substrate Conjugate to a Receptor

Directed binding of an activated substrate conjugate to the receptor results from the formation of a specific binding pair interaction. Members of specific binding pairs suitable for use in activated substrates binding to receptors can be of the immune or nonimmune type. Immune specific binding pairs are exemplified by antigen/antibody systems or hapten/antihapten systems. The antibody member, whether polyclonal, monoclonal or an immunoreactive fragment thereof, of the binding pair can be produced by customary methods familiar to those skilled in the art. The terms immunoreactive antibody fragment or immunoreactive fragment mean fragments which contain the binding region of the antibody. Such fragments may be Fab-type fragments which are defined as fragments devoid of the Fc portion, e.g., Fab, Fab' and F(ab')2 fragments, obtained by reductive cleavage of the disulfide bonds connecting the heavy chain components of the intact antibody.

Non-immune binding pairs include systems wherein the two components share a natural affinity for each other but are not antibodies. Exemplary non-immune binding pairs are pairs which form a covalent bond with each other. Exemplary covalent binding pairs include, but not limited to, dimerization of phenolic moieties (e.g., tyramine and tyrosine), sulfhydryl reactive groups such as maleimides and haloacetyl derivatives and amine reactive groups such as isothiocyanates, succinimidyl esters, sulfonyl halides and click chemistry and coupler dyes such as 3-methyl-2-benzothiazolinone hydrazone (MBTH) and 3-(dimethyl-amino) benzoic acid (DMAB).

E. Reporters or Labels

A wide variety of reporters (or labels) are available for coupling to the substrate to produce the substrate conjugate or to couple to a member of a specific binding pair. Reporters (or labels) can be but are not limited to enzymes, fluorescent, colorimetric, chemiluminescent, mass tags, magnetic, plasmonic or electrochemical materials.

In some embodiments, molecules that fluoresce may be used, such as organic small molecules, including, but not limited to, fluorophores, such as, but not limited to, fluorescein, rhodamine, cyanine dyes, Alexa dyes, DyLight dyes, Atto dyes, etc.

Chromogenic, fluorogenic and chemiluminescent materials may include, but not limited to, 3,3'-diaminobenzidine (DAB), nitro blue tetrazolium chloride (NBT), 5-bromo-4-chloro-3-indolyl phosphate (BCIP), and 5-bromo-4-chloro-3-indolyl-β-D-galactopyranoside (X-Gal).

In some embodiments, organic polymers, such as p-dots may be employed. In some embodiments, the observable moiety may be a biological molecule, including but not limited to a fluorescent protein or fluorescent nucleic acid (including fluorescent RNAs including Spinach and its derivatives). In some embodiments, the observable moiety may be an inorganic moiety including Q-dots. In some embodiments, the observable moiety may be a moiety that operates through scattering, either elastic or inelastic scattering, such as nanoparticles and Surface Enhanced Raman Spectroscopy (SERS) reporters (e.g., 4-Mercaptobenzoic acid, 2,7-mercapto-4-methylcoumarin). In some embodiments, the observable moiety may be chemiluminescence/ electrochemiluminescence emitters such as ruthenium complexes and luciferases. The observable moiety may generate an optical signal, an electromagnetic signal (across the entire electromagnetic spectrum), atomic/molecular mass (e.g. detectable by mass spectrometry), tangible mass (e.g., detectable by atomic force microscope), current or voltage.

F. Substrates

Substrates for use in substrate conjugate are specific for the enzymes chosen and are known to those skilled in the art. Many phenolic substrates have been described for use with horseradish peroxidase (U.S. Pat. Nos. 5,196,306, 5,583,001, 5,573,1158, 5,863,748 and 6,355,443), each of which are incorporated by reference for teaching of the phenolic substrates. Substrates for hydrolytic enzymes have also been described (U.S. Pat. Nos. 5,196,306, 5,583,001, 5,573,1158, 7,291,474, and Polaske, Bioconjugate Chemistry (2016)), each of which are incorporated by reference for teaching of the hydrolytic enzyme substrates.

Figure 6:
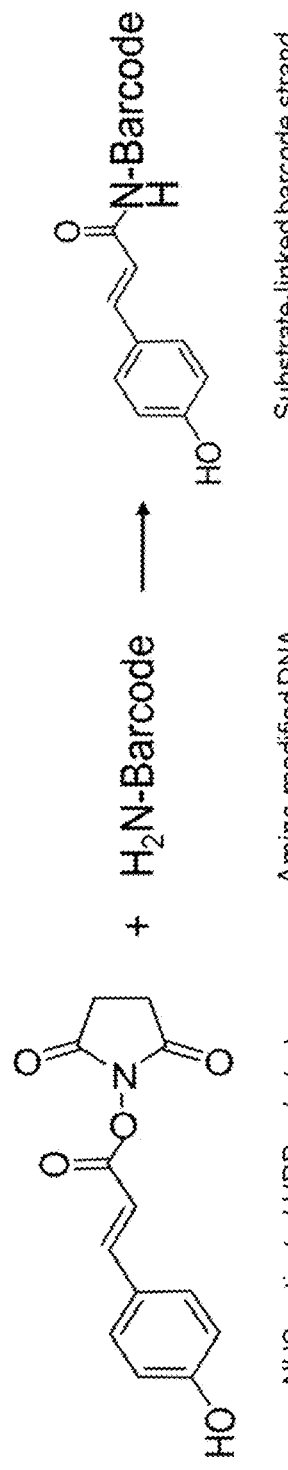
FIG. 6 shows a scheme for synthesizing an exemplary substrate-barcode.

In some embodiments, the enzyme is horseradish peroxidase (HRP) and the substrate is a phenolic substrate (e.g., tyramine (FIG. 6) and tyrosine). In some embodiments, the enzyme is a hydrolytic enzyme and the substrate is an ester, amide, or glycocide substrate.

G. Releasable Linkers

Throughout this disclosure, a first, second, or third releasable linker may be referred, yet in many embodiments some or all of them are optional. Merely referring to the second or third releasable linker does not require the presence of two or three releasable linkers. Instead, this numbering has been used throughout the application to name the linkers and differentiate them from each other. Thus, an embodiment comprising the second releasable linker does not necessarily have two releasable linkers and so on. This language only designates which linker is present, not how many linkers are present.

Releasable linkers are those that contain functionalities that can link two or more molecules such as proteins, nucleic acids, proteins to nucleic acids and substrates to detectable labels, as well as incorporate a bond that can be cleaved without heating or microwaving. Exemplary bonds that can be cleaved are disulfide bonds (cleaved by reducing agents such as dithiothreitol (DTI) or tris(2-carboxyethyl)phosphine (TCEP)), esters (cleaved by hydroxylamine), vicinal diols (cleaved by sodium meta-periodate), sulfones (cleaved under basic conditions), and photocleavable linkers such as those containing 2-nitrobenzyl groups.

An alternate method to using releasable linkers is to remove the enzyme or specific binding pair member bound to a nucleic strand in entirety. Removal may be facilitated by disrupting the binding affinities between the nucleic acid strands or by enzymatically cleaving unique nucleic acid sequences. Exemplary removal methods include USER enzyme (New England Biolabs), lowering the ionic strength of the medium, raising the temperature, and/or employing chaotropic agents such as guanidine, ethylene carbonate, and/or formamide.

In some embodiments, the releasable linker comprises a photocleavable linker that can be cleaved photochemically (e.g. by UV exposure, visible light, infrared, near infrared, x-ray, microwave, radio waves, or gamma rays). In some embodiments, the releasable linker contains a moiety that can be cleaved by an enzyme. Examples of such enzymatically cleavable moieties include but are not limited to ribonucleotides, which can be cleaved by a variety of RNases; deoxyuridines, which can be cleaved by enzyme combinations such as USER (New England Biolabs); and restriction sites, which can be cleaved by sequence-specific nicking enzymes or restriction enzymes. In some embodiments, the releasable linker comprises a deoxyuridine, in which the uracil group may be cleaved by uracil-DNA glycosylase. In some embodiments, the releasable linker comprises an abasic site, which may be cleaved by endonuclease.

1. Nucleic Acid-Degrading Enzymes

A number of enzymes can break the covalent bonds within a nucleic acid molecule. For example, some glycosylase can remove the base from the sugar moiety of a nucleotide, endonuclease can cut the bond within the phosphodiester bridge inside the nucleic acid molecule, while exonuclease can similarly break the phosphodiester bridge at the 5' or 3' terminal of the nucleic acid molecule in a sequential fashion. Another example comprises DNAzymes or deoxyribozymes, oligonucleotides with catalytic activity capable of cleaving the phosphodiester bond in nucleic acid molecules. All these types of enzymes may be engineered for releasing the releasable linkers and constitute enzymatically cleaving, modifying, or degrading the releasable linkers.

Glycosylase. If a glycosylase can specifically remove a base that participates the base-pairing, it can reduce the strength of interaction between the two strands. For example, one can use deoxyuridine (dU) to replace deoxythymidine in the releasable linker dU can pair with dA just like the dT does, but can be specifically removed by Uracil-DNA Glycosylase (UDG, commercially available from New England Biolabs, Cat #M0280S). This reaction will result in abasic site(s) on the nucleic acid strand linked to a detectable label. Such abasic sites can be further cleaved by Endonuclease VIII. This will further promote the dissociation between the remnant of binding pairs. Enzyme blend comprising both UDG and Endonuclease VIII is also commercially available (e.g., from New England Biolabs, under the tradename USER, Cat # M5505S). One may place from about 1 to 20, 1 to 15, 1 to 10, or 1 to 5 dU nucleotides in the nucleic acid strand linked to a detectable label. With USER, the dUs may be placed in a way that after removal of U, the remnants are short enough (e.g., less than or equal to about 9, 8, 7, 6, 5, 4, 3, 2, or 1 nucleotides) that they dissociate spontaneously and quickly. If only UDG (i.e., no Endonuclease VIII) is used, the removal of dU units could destabilize the strand enough to facilitate removal. Total number of base pairs between the binding pairs after dU removal may be less than or equal to 9, 8, 7, 6, 5, 4, 3, 2, or 1 nucleotides. Thus, in some embodiments the releasable linker may comprise at least one U capable of cleavage by USER.

The sequence of the remnants, as well as the temperature, will impact how short the remnants should be to dissociate spontaneously. For example, a sequence high in GC content might have more binding affinity at a shorter length than another sequence at a longer length. Thus, in some instances, a 9-mer may be sufficient for stable binding and in other instances a 9-mer may be sufficient to dissociate. A person of ordinary skill in the art can evaluate the sequences, temperatures, and affinities, here and in the cleavage of non-natural nucleotides discussed below.

Restriction endonuclease and nicking endonuclease. One may engineer a restriction site in the releasable linker. This allows the usage of the corresponding restriction endonuclease to cut such restriction site, which breaks the releasable linker. As an example, Cas9 (CRISPR associated protein 9) is an RNA-guided endonuclease that can be used to specifically cleave a releasable linker, by engineering a specific recognition site in the corresponding sequences.

This results in both strands being cleaved, preventing one from re-interrogating the corresponding target. To solve this problem, one can use nicking endonuclease which only cut one strand. As an example, Cas9 nickases are Cas9 enzymes that have been engineered to only include one active cleaving site, leading to single strand cuts, while conserving the high specificity of Cas9. Other examples of endonucleases with site specific activity include but are not limited to: zinc finger nucleases, transcription activator-like effector nucleases (TALENs), and deoxyribozymes.

Rnase. One may make some or all of nucleotides in the releasable linker RNA nucleotides (also called ribonucleotides), instead of DNA nucleotides (also called deoxynucleotide). Such RNA nucleotides can be removed by Rnase.

Polymerase. The releasable linker can also be removed by using polymerases with strand-displacement activity or 5'-to-3' exonuclease activity.

Cleavage of non-natural nucleotides. Non-natural nucleotide that serve as substrates for particular enzymes may be used. For example, 8-oxoguanine may be cleaved by DNA glycosylase OGG1. Abasic sites may also be incorporated into a DNA strand, such as a DNA strand linked to a detectable label, which may be cleaved by an endonuclease. For example, a 1',2'-Dideoxyribose, dSpacer, apurinic/apyrimidinic, tetrahydrofuran, or abasic furan may be cleaved by Endonuclease VIII. Thus, in some embodiments the nucleic acid strand linked to a detectable label or intermediate strand may comprise at least one abasic site capable of cleavage by Endonuclease VIII. In some embodiments the nucleic acid strand linked to a detectable label or intermediate strand may comprise at least one deoxyuridine and at least one abasic site capable of cleavage by USER, UDG, or Endonuclease VIII. Photocleavable spacers or RNA abasic sites may also be used, such as ribospacer (rSpacer) or Abasic II modification. Other pairs of non-natural nucleotides and their paired enzymes may be employed.

H. Enzyme Deactivation

An alternate method to using releasable linkers or removing the enzyme or specific binding pair member bound to a nucleic acid strand is to deactivate the enzyme. Exemplary enzyme deactivators include, but are not limited to, peroxides, reducing agents such as dithiothreitol (DTT), tris(2-carboxyethyl)phosphine (TCEP), and reduced glutathione, diisopropylfluorophosphate (DFP), α-difluoromethylornithine, fluoride salts, cyanide salts, azides, and specific binding pair members such as antibodies and aptamers.

In some embodiments, the enzyme is deactivated using an enzyme deactivator, wherein the enzyme deactivator comprises dithiothreitol (DTT), tris(2-carboxyethyl)phosphine (TCEP), a reduced glutathione, a peroxide, a cyanide, a fluoride, or an azide.

In some embodiments, deactivation of enzyme is performed for less than 20 minutes, less than 10 minutes, less than 5 minutes, less than 2 minutes, or less than or equal to 1 minute.

In some embodiments, deactivation of enzyme is performed by contacting the sample with an enzyme deactivator for less than 20 minutes, less than 10 minutes, less than 5 minutes, less than 2 minutes, or less than or equal to 1 minute.

I. Intermediate Moiety/Amplification/Pre-amplicon

In some instances, the nucleic acid strand linked to the target-specific binding partner binds to the nucleic acid strand linked to the enzyme through an intermediate moiety.

In some embodiments, the intermediate moiety is an intermediate strand comprising nucleic acids. In some embodiments, the nucleic acids are single stranded nucleic acids such as single stranded DNA, RNA, or a nucleic acid analog. A nucleic acid analog (also known as non-natural nucleic acid) may include an altered phosphate backbone, an altered pentose sugar, and/or altered nucleobases. Nucleic acid analogs may include, but are not limited to, 2'-O-Methyl ribonucleic acid, 2'-fluoro ribonucleic acid, peptide nucleic acid, morpholino and locked nucleic acid, glycol nucleic acid, and threose nucleic acid.

In some embodiments, the intermediate strand has a first region complementary to the nucleic acid strand linked to the target-specific binding partner and a second region complementary to the nucleic acid strand linked to the enzyme. In such embodiments, it is not necessary for the nucleic acid strand linked to the target-specific binding partner to be complementary to the nucleic acid strand linked to the enzyme.

In some embodiments, the intermediate strand and the nucleic acid strand linked to the target-specific binding partner are not added in discrete steps. In some instances, the intermediate strand and the nucleic acid strand linked to the target-specific binding partner are hybridized together before being added in a single step.

In some embodiments, the intermediate strand and the nucleic acid strand linked to the enzyme are not added in discrete steps. In some instances, the intermediate strand and the nucleic acid strand linked to the enzyme are hybridized together before being added in a single step.

In some embodiments, the intermediate strand is a premade amplicon comprising repeated sequences, each of the sequences capable of binding to a nucleic acid strand linked to an enzyme. In some embodiments, the intermediate strand is a first region complementary to a corresponding region of the nucleic acid strand linked to the target-specific binding partner, and a second region comprising repeated sequences, each of the sequences that specifically binds directly or indirectly to a corresponding sequence of the nucleic acid strand linked to an enzyme.

In some embodiments, the methods described herein further comprises amplifying the nucleic acid strand (or a portion thereof) directly or indirectly linked to the target-specific binding partner of step (1).

In some embodiments, the method described herein further comprises amplifying an intermediate moiety bound to the nucleic acid strand linked to the target-specific binding partner of step (1) by the primer exchange reaction (PER) described further below. In some embodiments, labeled nucleotides are used in the amplification reaction.

In some embodiments, the method described herein further comprises adding an intermediate moiety comprising repeat sequences. In some embodiments, the repeat sequences are produced using primer exchange reaction (PER) described herein. In some embodiments, the pre-amplicon is produced using rolling circle amplification (RCA) described herein.

1. Primer Exchange Reaction (PER)

PER can be used to prepare a nucleic acid product containing multiple probe-binding sites (i.e., intermediate moiety described herein); this nucleic acid product can then be bound to the nucleic acid (or a barcode domain thereof) linked to a target-specific binding partner; there the nucleic acid product may display probe-binding sites. In such embodiment, probe-binding sites may not be complementary to the barcode domain of the target specific binding partner.

Various PER and PER-based signal amplification methods have been described in Saka et al., "Highly multiplexed in situ protein imaging with signal amplification by Immuno-SABER" (2018; available as a preprint at www.biorxiv.org/content/10.1101/507566v1 as of Jun. 6, 2019); WO 2017/143006; and WO 2018/132392A2, the contents of each of which are herein incorporated by reference.

The PER reaction results in the formation of concatemer (repeats) sequences. The PER concatemer has a first domain that is complementary to the nucleic acid strand linked to the target-specific binding partner and a second domain comprising repeat sequences. The repeated sequence may be the same as the nucleic acid strand linked to the target-specific binding partner. The repeated sequence may be different from the nucleic acid strand linked to the target-specific binding partner.

IV. Supporting Information on Methods of Multiplex Imaging

A. Spectral and Sequential Multiplexing

Two main methods exist for creating multiplexing in exchange imaging: spectral multiplexing and sequential multiplexing. Spectral multiplexing refers to the ability to use different labels (such as different fluorophores) in a single round of imaging. Spectral multiplexing does not necessitate extinguishing the signal from the first label before viewing the second label. For example, in the case of fluorophores, different excitation wavelengths of light can be used to individually excite different fluorophores. This does not require separate rounds of imaging. Sequential multiplexing refers to the ability to use the same labels (such as the same fluorophore) in multiple rounds of imaging by extinguishing the signal from the first round of imaging before the second round of imaging. Spectral multiplexing and sequential multiplexing can either be used alone or in conjugation with each other. Using more than one technique of multiplexing, however, can significantly increase the number of targets that a user can visualize during a particular experiment.

In some embodiments, multiple rounds of imaging are performed with at least some of the same fluorophores. For example, in a first round of imaging, target A can be imaged with label X, target B can be imaged with label Y, and target C can be imaged with label Z. As a next step, the signals from these labels can be extinguished. Then, in a second round of imaging, target D can be imaged with label X, target E can be imaged with label Y, and target F can be imaged with label Z. Item In some embodiments, at least two targets are imaged using at least two labels, the signal extinguished, and then at least one more target is imaged using at least one of the same labels, wherein the imaging steps may be performed in either order. This means that the order of steps could be reversed so the first imaging step comprises imaging at least one target, the signal extinguished, and the second imaging step comprises imaging at least two targets.

Combining both spectral multiplexing and sequential multiplexing can increase the overall convenience of performing the imaging for the user and reduce disruption to the sample being imaged.

B. Control Experiments and Background Subtraction

Control experiments and background subtraction may be employed to further improve the results of the methods of testing a sample for the presence of one or more targets. Neither of these aspects are required for useful experimentation; however, both improve the quality of multiplexing and can be used alone or in conjunction with each other.

1. Control Experiments

Control measurements may be added at multiple time points in a multiplexed process by performing a control step by contacting the sample with a binding pair having a nucleotide sequence that is not complementary to a nucleic acid strand, bound to the target-specific binding partner (or a portion thereof, such as a barcode).

2. Background Subtraction

In any of the embodiments discussed throughout this application, the method may employ background subtraction. In some embodiments, the method comprises imaging the sample to detect and/or measure a background signal and subtracting the background signal from the image of the sample to detect bound labels. Such background signals may include autofluorescence and/or residual fluorescence associated with incompletely extinguishing signal from the bound labels. In some embodiments, the background signal is measured before the image of the sample to detect bound labels. In other embodiments, the background signal is measured after the image of the sample to detect bound labels.

C. Description of Samples

1. Types of Samples

Various types of samples may be imaged using these methods. In some embodiments, the sample is a fixed sample. In some embodiments, the sample is a cell, cell lysate, tissue, tissue lysate, and or a whole organism. In some embodiments, the sample is a cell or tissue sample, a cell or tissue lysate, or a bodily fluid. In some embodiments, the sample is tissue and the imaging comprises in-tissue multiplexing for immunostaining.

The sample may be provided in a liquid medium or buffer solution.

2. Antigen Retrieval

In some embodiments, staining a sample with a target-specific binding partner requires specific conditions and not all target-specific binding partners will bind to their antigens under the same conditions. This may be because their target antigens are not available under the same conditions.

3. Description of Targets and Use in Identifying Biomarkers

In some embodiments, the method is useful for identifying a biomarker. In some instances, samples are imaged and data analysis performed on those samples. In some embodiments, multiple targets are tested for using corresponding target-specific binding partners for each target. In some instances, the relationship between different targets may be assessed; for example, a user might seek to determine the relationship of multiple markers to a disease state and conclude that the disease sample has increased levels of A, decreased levels of B, and levels of C within a certain range, as compared to healthy tissue that does not have that biomarker distribution.

In some embodiments, at least 10, 96, 100, 384, or 500 samples are imaged and data analysis performed on those samples.

In some embodiments, at least 5, 10, 15, 25, 30, 50, 75, or 100 or more targets are tested for using corresponding target-specific binding partners for each target.

D. Equipment and Software

1. Imaging Chamber, Such as a Flow Cell

In some embodiments, an imaging chamber can be employed. In some instances, an imaging chamber is a fixed chamber with no inlet and no outlet. In some embodiments, an imaging chamber has a single inlet/outlet combination. In other instances, an imaging chamber allows for flow and is designated a flow cell. A flow cell may be comprised of a first optically transparent support in combination with a second optically transparent material (such as a glass or plastic coverslip) to provide a flow cell with a top and bottom surface and fluid flow between them. If a first and second optically transparent material are used, they may be placed parallel to each other. By parallel, it includes geometrical arrangements that are perfectly parallel, as well as those that deviate from parallel by up to 1°, 2°, 3°, 4°, 5°, 6°, 7°, 8°, 9°, or 10°. In some embodiments, the second optically transparent material is in close proximity to the first optically transparent material, such as about 5 microns to 5 mm, from 50 microns to 500 microns, or from 500 microns to 5 mm.

An imaging chamber may also be comprised of a first optically transparent support and a gasket (also referred to as an isolator or spacer). The gasket may be open to the air on the top surface or it may be closed and have an optically transparent top surface. The gasket may have a combined inlet/outlet or it may have both an inlet and an outlet. The gasket may also have no outlet. The gasket may be plastic, rubber, adhesive. A gasket may comprise a CoverWell Chamber Gasket (Thermo Fisher), an ultra-thin sealed chamber for upright and inverted microscopes (Bioscience Tools), or an incubation chamber (Grace Bio-Labs, including HybriSlip™ hybridization covers, HybriWell™ sealing system, CoverWell™ incubation chambers, imaging spacers, SecureSeal™ hybridization chambers, FlexWell™ incubation chambers, FastWells™ reagent barriers, and Silicone Isolators™).

In some instances, a gasket may be employed along with a coverslip forming the top surface of an imaging chamber or flow cell.

Imaging chambers, such as but not limited to flow cells, may be reusable or disposable.

2. Software for Control of Fluidic Steps

In some embodiments, all fluidic exchange steps are performed using a fluidic system comprising electronic, and/or pneumatic, and/or hydraulic, and/or electro-fluidic actuators and systems. In certain situations, the fluidic system is controlled by software. In some embodiments, wherein the fluidic system is automatically controlled by software synchronizing the preceding step(s) of the method described in the preceding paragraphs with the imaging step.

In some embodiments, the fluidic system is controlled by software synchronizing the preceding step(s) of the method with the imaging step by communicating with the imaging software, with the references to step numbers described in the preceding paragraphs.

In some embodiments, all fluidic steps are performed while the sample is on the imaging device.

The sample may be fixed in a disposable imaging chamber (such as a flow cell), a reusable imaging chamber (such as a flow cell), a slide, a slide with a coverslip, or any other configuration.

EXAMPLES

Example 1. Deposition of Fluorescent Reporter Through HRP Cycling

Four different targets, CD8, CD68, PD-L1, and CK, were labeled using sequential deposition of respective fluorescent tyramide reagents. Specifically, formalin-fixed paraffin-embedded (FFPE) tissue slides were baked then loaded onto a BOND RX autostainer (Leica Biosystems, Nussloch GmbH) for all subsequent steps. Slides were dewaxed and antigen retrieved using Epitope Retrieval Solution 2 BOND (Leica Biosystems). Endogenous peroxidase activity was quenched with 3% $H_2O_2$, then blocked with antibody diluent (Ultivue, Cambridge, Mass.) at room temperature for 15 minutes. A mixture of four different primary antibodies (anti-CD8, anti-CD68, anti-PD-L1, and anti-CK) conjugated to nucleic acid barcodes and diluted in antibody diluent was incubated with the tissue sample for 30 min at room temperature. Samples were washed with BOND Wash Solution (Leica Biosystems) then incubated with a preamplification mix (Ultivue) for 10 min at room temperature, followed by additional washing steps. Samples were incubated with amplification solution (Ultivue) for 15-20 min, then washed. A first set of nucleic acid probe strands, complementary to the anti-CD8 antibody conjugate, and linked to HRP enzymes via a disulfide bond was added to the sample and allowed to hybridize to its partner strand for 15 min Unbound HRP coupled probes were removed with a washing step. A working solution of Alexa Fluor™ 488 Tyramide Reagent (Invitrogen™) was applied to the tissue sample according to package instructions to label CD8 targets. The HRP enzymes linked to the first set of nucleic acid probe strands were deactivated from the sample by the addition of a TCEP solution in Tris buffer for 1 minute. Following deactivation of the HRP enzymes associated with the first round of CARD, a second set of nucleic acid probe strands, complementary to the anti-CD68 antibody conjugate, linked to HRP enzymes via a disulfide bond was added to the sample and allowed to hybridize to its partner strand. Unbound HRP coupled probes were removed with a washing step. A working solution of Alexa Fluor™ 555 Tyramide Reagent (Invitrogen) was applied to the tissue sample according to package instructions to label CD68 targets. The HRP enzymes linked to the second set of nucleic acid probe strands were deactivated from the sample by the addition of a TCEP solution in Tris buffer for 1 minute. Following deactivation of the HRP enzymes associated with the second round of CARD, a third set of nucleic acid probe strands, complementary to the anti-PD-L1 antibody conjugate, linked to HRP enzymes via a disulfide bond was added to the sample and allowed to hybridize to its partner strand. Unbound HRP coupled probes were removed with a washing step. A working solution of Alexa Fluor™ 647 Tyramide Reagent (Invitrogen) was applied to the tissue sample according to package instructions to label PD-L1 targets. The HRP enzymes linked to the third set of nucleic acid probe strands were deactivated from the sample by the addition of a TCEP solution in Tris buffer for 1 minute. Following deactivation of the HRP enzymes associated with the third round of CARD, a fourth set of nucleic acid probe strands, complementary to the anti-CK antibody conjugate, linked to HRP enzymes via a disulfide bond was added to the sample and allowed to hybridize to its partner strand. Unbound HRP coupled probes were removed with a washing step. A working solution of Alexa Fluor™ 750 Tyramide Reagent (Invitrogen) was applied to the tissue sample according to package instructions to label CK targets. A nuclear counterstain was applied to the slides and samples were coverslipped and imaged with a fluorescence microscope.

Figure 7:
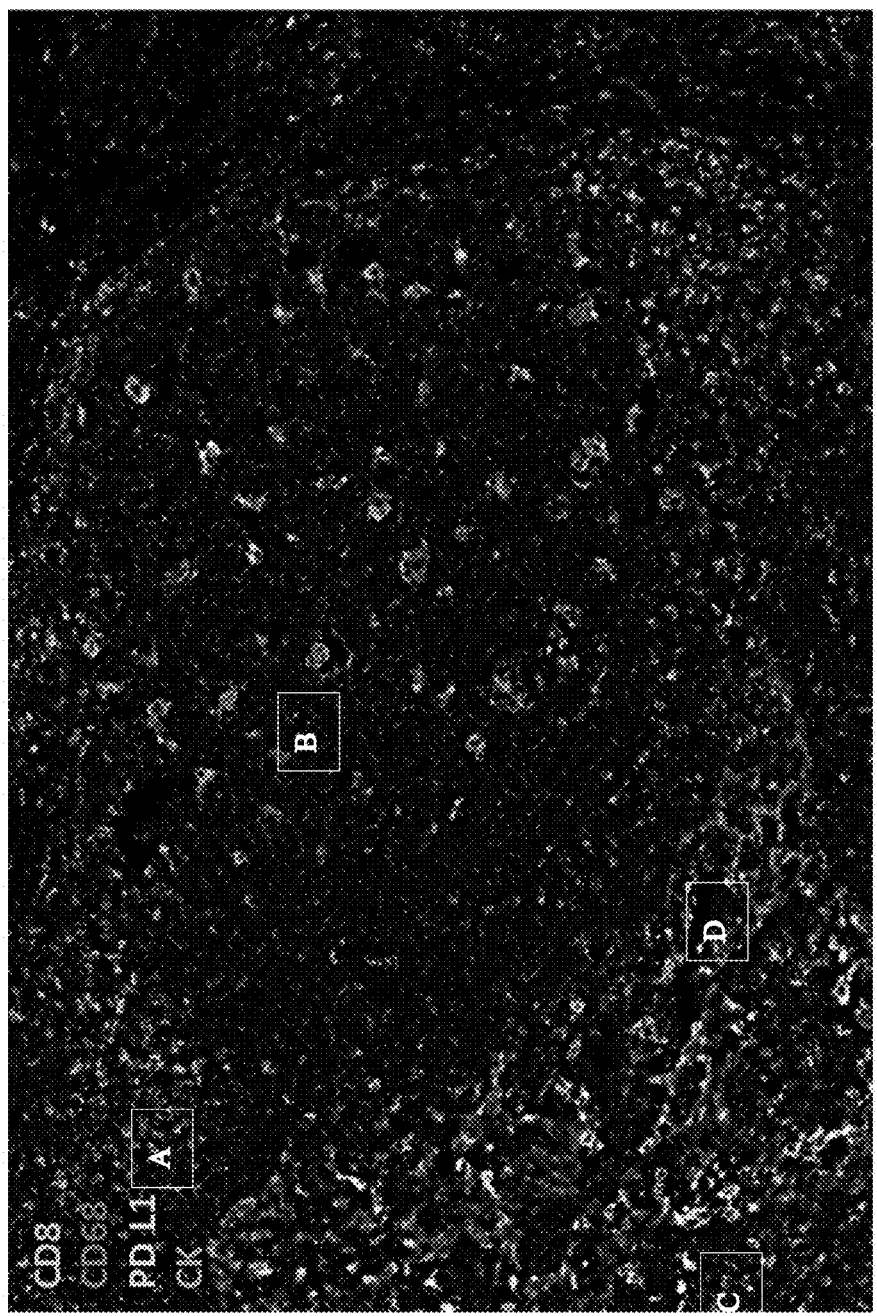
FIG. 7 shows a four-plex image of CD8, CD68, PD-L1, and CK targets (nuclear counterstain not shown) acquired using sequential deposition of fluorescent tyramide reagents according to Example 1. CD8 is shown as green; CD68 is shown as red; PD-L1 is shown in cyan; CK is shown in magenta. The nuclear counterstain is not shown.

FIG. 7 shows that the four targets-CD8, CD68, PD-L1, and CK, were successfully labeled using sequential deposition of the respective fluorescent reporters. Box A shows exemplary location of labeled CD8; Box B for labeled CD68; Box C for labeled PD-L1; Box D for labeled CK.

Example 2. Deactivation of HRP for Cyclic Deposition

To achieve cyclic deposition of labels using an HRP-based enzymatic reaction, the HRP enzymes need to be removed or deactivated between successive deposition rounds. HRP enzymes may be deactivated through heat or pH based denaturing, or cleaved off of the sample through a labile linker (FIG. 4A). In this example, HRP enzymes were deactivated, in the absence of any labile linkers, using reducing agents (FIG. 4B).

FFPE tissue slides were baked at 60° C. for 30 minutes, then dewaxed and antigen retrieved with Epitope Retrieval Solution 2 BOND (Leica Biosystems)on a BOND RX autostainer (Leica Biosystems). Slides were removed from the BOND RX for subsequent steps. Endogenous peroxidase activity was quenched using 3% $H_2O_2$ for 20 min, washed in PBS, then blocked with antibody diluent (Ultivue, Cambridge, Mass.) for 15 min at room temperature. Primary antibodies (from Example 1) conjugated to nucleic acid barcodes were diluted in antibody diluent and incubated with the tissue sample for 1 hour at room temperature. Samples were washed and incubated with a preamplification mix (Ultivue) for 25 min at room temperature, followed by additional washing steps. Samples were incubated with amplification solution (Ultivue) for 15 min at 30° C., then washed in PBS. A first set of nucleic acid probe strands, complementary to one of the antibody-conjugated nucleic acid barcodes, linked to HRP enzymes (without a disulfide bridge) was added to the sample and allowed to hybridize to its partner strand. Unbound HRP coupled probes were removed with a washing step. Tissue slides were exposed either to a TCEP solution for 5 minutes to deactivate the HRP or to Tris buffer as a control. A working solution of Alexa Fluor™ 647 Tyramide (Invitrogen) was added to all slides, incubated for 10 min at room temperature, and washed away in PBS. Finally, slides were stained with a nuclear counterstain, washed, and coverslipped. Slides were imaged on a fluorescence microscope.

Figure 8:
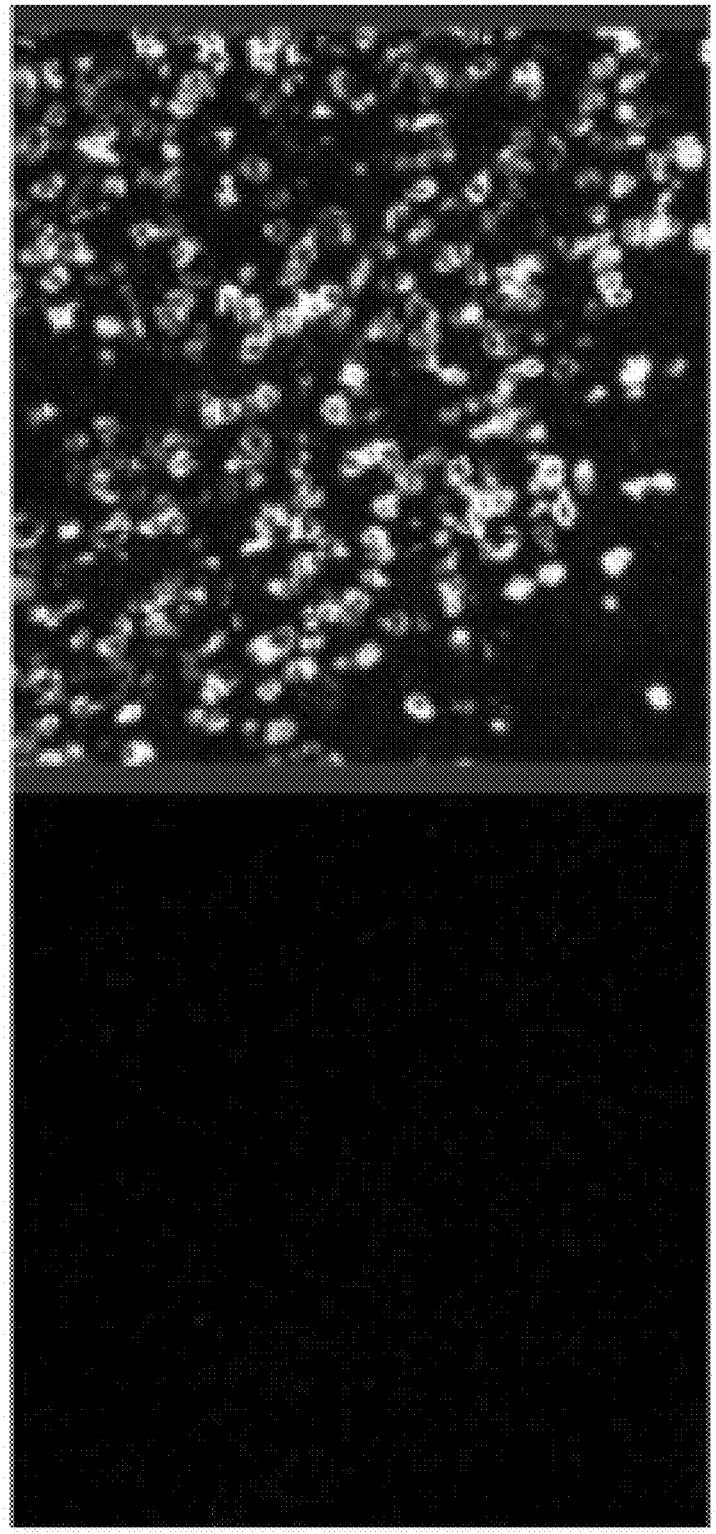
FIGS. 8A-8B show comparison of deactivation of HRP enzyme with TCEP treatment (FIG. 8A) versus a control without TCEP treatment (FIG. 9B) according to Example 2.

FIGS. 8A-8B show that samples treated with TCEP solution prior to deposition of the tyramide reagent did not result in tyramide deposition, whereas the tyramide reagent was successfully deposited in control samples that were not exposed to TCEP. This surprising result indicates that the TCEP solution deactivated the HRP enzyme.

Example 3. Deposition of Binding Pairs Through HRP Cycling

Figure 5:
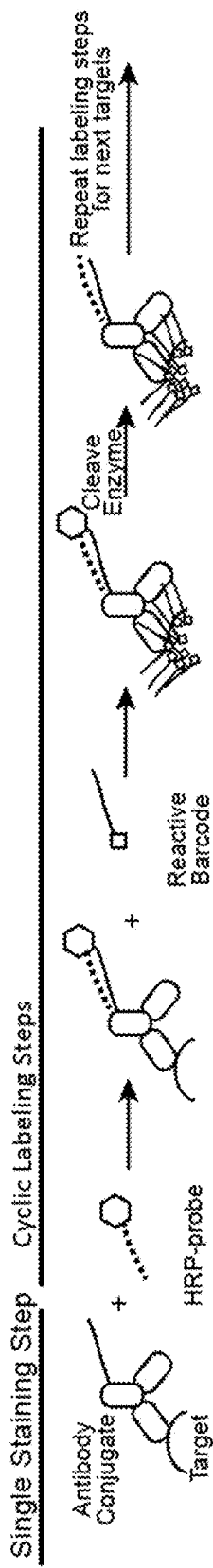
FIG. 5 shows an exemplary embodiment in which substrate-barcodes are used.

FFPE tissue slides were baked and then loaded onto a BOND RX autostainer (Leica Biosystems) for all subsequent steps. Slides were dewaxed and antigen retrieved using Epitope Retrieval Solution 2 BOND (Leica Biosystems). Endogenous peroxidase activity was quenched using 3% $H_2O_2$, then blocked with antibody diluent (Ultivue, Cambridge, Mass.) at room temperature for 15 minutes. A mixture of four different primary antibodies (anti-CD8, anti-CD68, anti-PD-L1, and anti-CK) conjugated to nucleic acid barcodes and diluted in antibody diluent was incubated with the tissue sample for 30 min at room temperature. Samples were washed, then incubated with a preamplification mix (Ultivue) for 10 min at room temperature, followed by additional washing steps. Samples were incubated with amplification solution (Ultivue) for 15-25 min, then washed. A first set of nucleic acid probe strands, complementary to the anti-CD8 antibody conjugate, and linked to HRP enzymes via a disulfide bond was added to the sample and allowed to hybridize to its partner strand for 15 min Unbound HRP coupled probes were removed with a washing step. A working solution of nucleic acid barcodes linked to a phenol HRP reactive substrate (FIG. 6) was applied to the tissue sample to deposit additional nucleic acid barcodes at the site of CD8 targets (e.g., depicted in FIG. 5). The HRP enzymes linked to the first set of nucleic acid probe strands were deactivated from the sample by the addition of a TCEP solution in Tris buffer for 1 minute. Following deactivation of the HRP enzymes associated with the first round of CARD, a second set of nucleic acid probe strands, complementary to the anti-CD68 antibody conjugate, linked to HRP enzymes via a disulfide bond was added to the sample and allowed to hybridize to its partner strand. Unbound HRP coupled probes were removed with a washing step. A working solution of nucleic acid barcodes linked to a phenol HRP reactive substrate was applied to the tissue sample to deposit additional nucleic acid barcodes at the site of CD68 targets. The HRP enzymes linked to the second set of nucleic acid probe strands are deactivated from the sample by the addition of a TCEP solution in Tris buffer for 1 minute. Following deactivation of the HRP enzymes associated with the second round of CARD, a third set of nucleic acid probe strands, complementary to the anti-PD-L1 antibody conjugate, linked to HRP enzymes via a disulfide bond is added to the sample and allowed to hybridize to its partner strand. Unbound HRP coupled probes were removed with a washing step. A working solution of nucleic acid barcodes linked to a phenol HRP reactive substrate was applied to the tissue sample to deposit additional nucleic acid barcodes at the site of PD-L1 targets. The HRP enzymes linked to the third set of nucleic acid probe strands were deactivated from the sample by the addition of a TCEP solution in Tris buffer for 1 minute. Following deactivation of the HRP enzymes associated with the third round of CARD, a fourth set of nucleic acid probe strands, complementary to the anti-CK antibody conjugate, linked to HRP enzymes via a disulfide bond was added to the sample and allowed to hybridize to its partner strand. Unbound HRP coupled probes were removed with a washing step. A working solution of nucleic acid barcodes linked to a phenol HRP reactive substrate was applied to the tissue sample to deposit additional nucleic acid barcodes at the site of CK targets. Samples were washed and a mixture of fluorescently labeled probe strands, with complementarity to the nucleic acid barcodes, was allowed to hybridize to the sample. Unbound fluorescently labeled probe strands were removed and a nuclear counterstain was applied to the slides. Samples were coverslipped and imaged with a fluorescence microscope.

Figure 9:
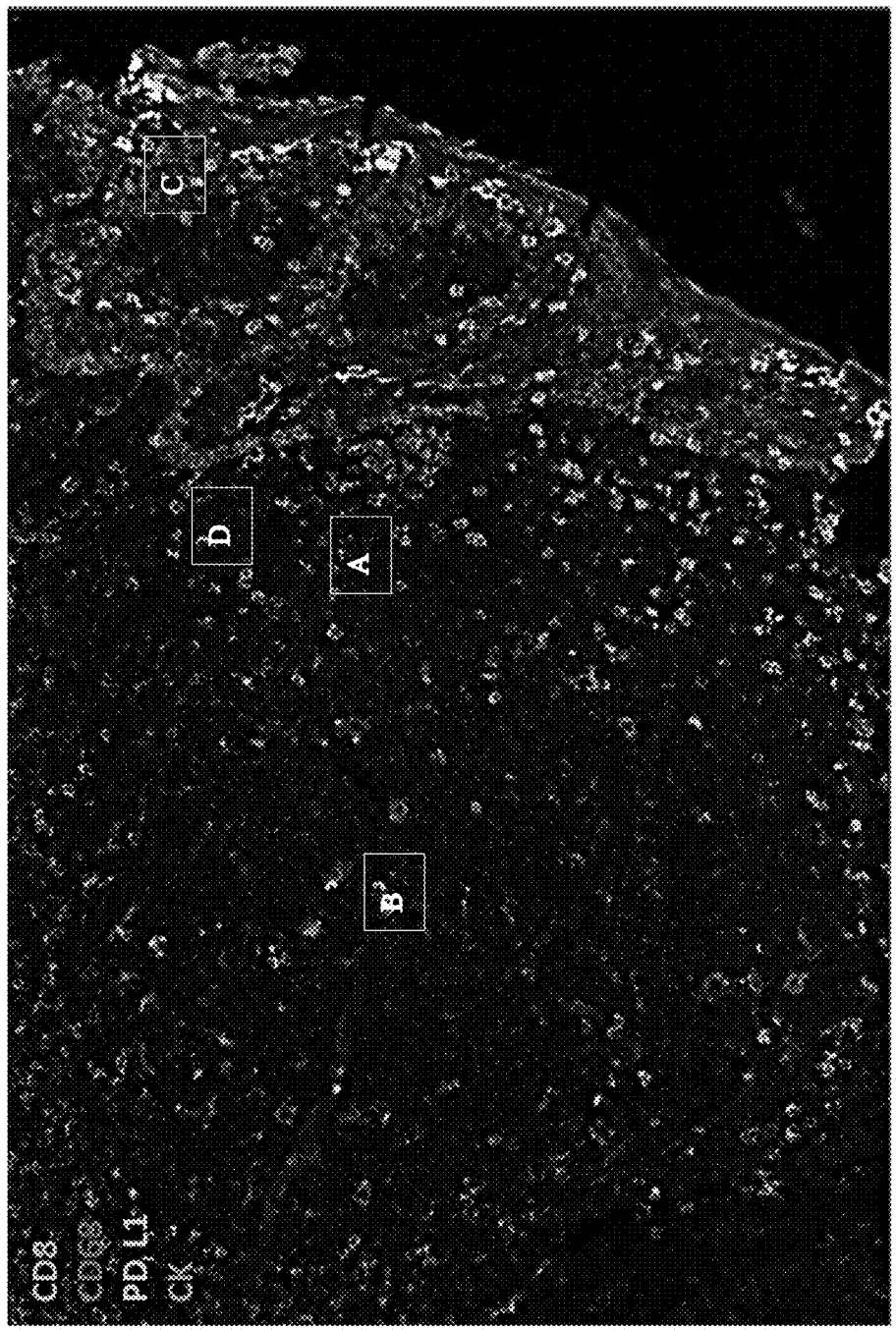
FIG. 9 shows a four-plex image of CD8, CD68, PD-L1, and CK targets acquired using sequential deposition of nucleic acid barcodes according to Example 3. CD8 is shown as green; CD68 is shown as red; PD-L1 is shown in cyan; CK is shown in magenta. The nuclear counterstain is not shown.

FIG. 9 shows that the four targets-CD8, CD68, PD-L1, and CK, were successfully labeled using sequential deposition of the respective fluorescent reporters. Box A shows exemplary location of labeled CD8; Box B for labeled CD68; Box C for labeled PD-L1; Box D for labeled CK.

Example 4. ADDITIONAL EMBODIMENTS

The following numbered items provide additional support for and descriptions of the embodiments herein.

Item 1. A method for testing a sample for the presence of one or more targets comprising
  (1) contacting a sample being tested for the presence of one or more targets with one or more target-specific binding partners, wherein each target-specific binding partner is linked to a nucleic acid strand and wherein target-specific binding partners of different specificity are linked to different nucleic acid strands;
  (2) optionally removing unbound target-specific binding partners;
  (3) contacting the sample from step (1) or optionally step (2) with an enzyme linked to a nucleic acid strand complementary to the nucleic acid strand linked to the target-specific binding partner, wherein the following (i) or (ii) or both is met:
  (i) the nucleic acid strand is linked to the target-specific binding partner with a first releasable linker; and
  (ii) the enzyme is linked to the complementary nucleic acid strand with a second releasable linker;
(4) optionally removing unbound enzyme linked to complementary nucleic acid strands;
(5) contacting the sample from step (3) or optionally step (4) with a substrate conjugate comprised of a detectably labeled substrate, where the substrate and detectable label are linked optionally with a third releasable linker;
(6) optionally removing unbound substrate conjugate;
(7) optionally releasing the bound enzyme;
(8) imaging the sample to detect the bound detectable labels; and
(9) optionally repeating steps (1)-(8) or any subset thereof.

Item 2. The method of item 1, wherein in step (5), the substrate conjugate comprised of the detectably labeled substrate reacts with the enzyme to form an activated substrate conjugate, and the activated substrate conjugate binds to a receptor for the activated substrate conjugate.

Item 3. The method of item 2, wherein the receptor for the activated substrate conjugate is immobilized on a solid support, resulting in the deposition of the detectable labels.

Item 4. The method of item 1, further comprising (10) optionally releasing the bound detectable labels after step (8) by releasing the third releasable linker and optionally repeating steps (1)-(10) or any subset thereof.

Item 5. A method for testing a sample for the presence of one or more targets comprising
  (1) contacting a sample being tested for the presence of one or more targets with one or more target-specific binding partners, wherein each target-specific binding partner is linked to a nucleic acid strand and wherein target-specific binding partners of different specificity are linked to different nucleic acid strands;
  (2) optionally removing unbound target-specific binding partners;
  (3) contacting the sample from step (1) or optionally step (2) with a first member of a binding pair linked to a nucleic acid strand complementary to the nucleic acid strand linked to the target-specific binding partner, wherein the following (i) or (ii) or both is met:
    (i) the nucleic acid strand is linked to the target-specific binding partner with a first releasable linker; and
    (ii) the first member of the binding pair is linked to the complementary nucleic acid strand with a second releasable linker;
  (4) optionally removing unbound first member of binding pair linked to complementary nucleic acid strands;
  (5) contacting the sample from step (3) or optionally step (4) with a second member of the binding pair linked to an enzyme optionally with a third releasable linker, and optionally removing unbound second member of the binding pair linked to the enzyme;
  (6) contacting the sample from step (5) with a substrate conjugate comprised of a labeled substrate, where the substrate and label are linked optionally with a fourth releasable linker;
  (7) optionally removing unbound substrate conjugate;
  (8) optionally releasing the bound first or second member of the binding pair;
  (9) imaging the sample to detect the bound detectable labels; and
  (10) optionally repeating steps (1)-(9) or any subset thereof.

Item 6. The method of item 5, further comprising (11) optionally releasing the bound detectable labels after step (9) by cleaving the third releasable linker between the label and the substrate, and optionally repeating steps (1)-(11) or any subset thereof.

Item 7. A method for testing a sample for the presence of one or more targets comprising:
  (1) contacting a sample being tested for the presence of one or more targets with one or more target-specific binding partners, wherein each target-specific binding partner is linked to a nucleic acid strand and wherein target-specific binding partners of different specificity are linked to different nucleic acid strands;
  (2) optionally removing unbound target-specific binding partners;
  (3) contacting the sample from step (1) or optionally step (2) with an enzyme linked to a nucleic acid strand complementary to the nucleic acid strand linked to the target-specific binding partner, wherein the following (i) or (ii) or both is met:
    (i) the nucleic acid strand is linked to the target-specific binding partner with a first releasable linker; and
    (ii) the enzyme is linked to the complementary nucleic acid strand with a second releasable linker;
  (4) optionally removing unbound enzyme linked to complementary nucleic acid strands;
  (5) contacting the sample from step (3) or optionally step (4) with a substrate conjugate comprised of a nucleic acid strand-bound substrate, where the substrate and nucleic acid strand are linked optionally with a third releasable linker;
  (6) optionally removing unbound substrate conjugate;
  (7) optionally releasing the bound enzymes;
  (8) contacting the sample from step (5) or optionally steps (6)-(7) with a nucleic acid strand-bound detectable label, linked optionally with a fourth releasable linker, where the nucleic acid strand is a specific binding pair member to the nucleic acid strand in step (5);
  (9) optionally imaging the sample to detect the bound labels;
  (10) optionally releasing the bound label from step (8) by releasing the releasable linker of step (5) or optionally step (8) or optionally steps (5) and (8); and
  (11) optionally repeating steps (1)-(10) or any subset thereof.

Item 8. A method for testing a sample for the presence of one or more targets comprising:
  (1) contacting a sample being tested for the presence of one or more targets with one target-specific binding partner, wherein the target-specific binding partner is linked to a nucleic acid strand,
  (2) optionally removing unbound target-specific binding partners,
  (3) contacting the sample with the horseradish peroxidase (HRP) enzyme-bound nucleic acid strand, complementary to the nucleic acid strand linked to the target-specific binding partner, wherein the following (i) or (ii) or both is met:
    (i) the nucleic acid strand is linked to the target-specific binding partner with a first releasable linker; and
    (ii) the HRP is linked to the complementary nucleic acid strand with a second releasable linker;

(4) optionally removing unbound enzymes linked to complementary nucleic acid strands;
(5) contacting the sample from step (3) or optionally step (4) with a substrate conjugate comprised of a detectably labeled phenol-including substrate, where the substrate and the detectable label are linked optionally with a third releasable linker;
(6) optionally removing unbound substrates;
(7) imaging the sample to detect the bound detectable labels;
(8) optionally releasing the bound detectable labels; and
(9) optionally repeating steps (1)-(8) or any subset thereof.

Item 9. The method of item 8, wherein after step (5), the phenol moiety is enzymatically converted into an activated state resulting in the deposition of the labels.

Item 10. The method of any one of items 1-9, wherein the releasable linkers includes at least one of disulfide bonds, esters, vicinal diols, sulfones, and photocleavable linkers.

Item 11. The method of any one of items 1-10, wherein the enzyme is chosen from oxidoreductases, hydrolases, lyases, transferases, isomerases, and ligases.

Item 12. The method of any one of items 1-11, wherein the enzyme is chosen from peroxidases, oxidases, phosphatases, esterases and glycosidases.

Item 13. The method of item 12, wherein the enzyme is chosen from horseradish peroxidase, glucose oxidase, alkaline phosphatase and beta-galactosidase.

Item 14. The method of item 13, wherein the enzyme is horseradish peroxidase.

Item 15. The method of any one of items 1-14, wherein the binding pair is immune type or nonimmune type.

Item 16. The method of item 15, wherein the immune type binding pair is chosen from antigen-antibody and hapten-antihapten.

Item 17. The method of item 16, wherein the antibody member of the binding pair is polyclonal, monoclonal or an immunoreactive fragment thereof.

Item 18. The method of item 15, wherein the nonimmune type binding pair is chosen from biotin-avidin, biotin-streptavidin, and complementary probe nucleic acids folic acid-folate binding protein.

Item 19. The method of item 18, wherein the nonimmune type binding pair form a covalent bond via sulfhydryl reactive groups (e.g., maleimides and haloacetyl derivatives), amine reactive groups (e.g., isothiocyanates, succinimidyl esters, sulfonyl halides, click chemistry), and coupler dyes (e.g., 3-methyl-2-benzothiazolinone hydrazone (MBTH) and 3-(dimethyl-amino)benzoic acid (DMAB)).

Item 20. The method of any one of items 1-19, wherein the detectable label is chosen from enzymes, radioactive isotopes, fluorogenic, chemiluminescent, and electrochemical materials.

Item 21. The method of any one of items 1-20, wherein the enzyme is horseradish peroxidase (HRP) and the substrate is a phenolic substrate.

Item 22. The method of any one of items 1-21, wherein the enzyme is a hydrolytic enzyme and the substrate is an ester, amide, or glycocide substrate.

Item 23. A composition comprising:
(1) a sample bound to more than one target-specific binding partners, each binding partner bound to a nucleic acid strand,
(2) an enzyme to a nucleic acid strand complementary to the nucleic acid strand bound to the target-specific binding partner, wherein the following (i) or (ii) or both is met:
    (i) the nucleic acid strand is linked to the target-specific binding partner with a first releasable linker; and
    (ii) the enzyme is linked to the complementary nucleic acid strand with a second releasable linker; and
(3) a substrate conjugate comprised of a detectably labeled substrate, where the substrate and label are linked optionally with a third releasable linker.

Item 24. A composition comprising:
(1) a sample bound to more than one target-specific binding partners, each binding partner bound to a nucleic acid strand,
(2) a binding pair comprising:
    (i) a first member linked to a nucleic acid strand complementary to the nucleic acid strand bound to the target-specific binding partner, and
    (ii) a second member linked to an enzyme,
wherein the following (i) or (ii) or both is met:
    (i) the nucleic acid strand is linked to the target-specific binding partner with a first releasable linker; and
    (ii) the first member of the binding pair is linked to the complementary nucleic acid strand with a second releasable linker; and
(3) a substrate conjugate comprised of a detectably labeled substrate, where the substrate and label are linked optionally with a third releasable linker, wherein the second member of the binding pair is linked to the enzyme with a fourth releasable linker.

Item 25. A composition comprising:
(1) a sample bound to more than one target-specific binding partners, each binding partner bound to a nucleic acid strand,
(2) an enzyme linked to linked to a nucleic acid strand complementary to the nucleic acid strand bound to the target-specific binding partner,
wherein the following (i) or (ii) or both is met:
    (i) the nucleic acid strand is linked to the target-specific binding partner with a first releasable linker; and
    (ii) the enzyme is linked to the complementary nucleic acid strand with a second releasable linker; and
(3) a substrate conjugate comprised of a nucleic acid strand-bound substrate, where the substrate and nucleic acid strand are linked optionally with a third releasable linker;
(4) a nucleic acid strand-bound detectable label, linked optionally with a fourth releasable linker, where the nucleic acid strand of (4) is a specific binding pair member to the nucleic acid strand of (3).

Item 26. A method for testing a sample for the presence of one or more targets comprising
(1) contacting a sample being tested for the presence of one or more targets with one or more target-specific binding partners, wherein each target-specific binding partner is linked to a nucleic acid strand and wherein target-specific binding partners of different specificity are linked to different nucleic acid strands;
(2) optionally removing unbound target-specific binding partners;
(3) contacting the sample from step (1) or optionally step (2) with an enzyme linked to a nucleic acid strand complementary to the nucleic acid strand linked to the target-specific binding partner;
(4) optionally removing unbound enzyme linked to complementary nucleic acid strands;
(5) contacting the sample from step (3) or optionally step (4) with a substrate conjugate comprised of a detectably labeled substrate, where the substrate and detectable label are linked optionally with a releasable linker;

(6) optionally removing unbound substrate conjugate;
(7) optionally deactivating the bound enzyme;
(8) optionally imaging the sample to detect the bound detectable labels; and
(9) optionally repeating steps (1)-(8) or any subset thereof.

Item 27. A method for testing a sample for the presence of one or more targets comprising
(1) contacting a sample being tested for the presence of one or more targets with one or more target-specific binding partners, wherein each target-specific binding partner is linked to a nucleic acid strand and wherein target-specific binding partners of different specificity are linked to different nucleic acid strands;
(2) optionally removing unbound target-specific binding partners;
(3) contacting the sample from step (1) or optionally step (2) with a first member of a binding pair linked to a nucleic acid strand complementary to the nucleic acid strand linked to the target-specific binding partner,
(4) optionally removing unbound first member of binding pair linked to complementary nucleic acid strands;
(5) contacting the sample from step (3) or optionally step (4) with a second member of the binding pair linked to an enzyme and optionally removing unbound second member of the binding pair linked to the enzyme;
(6) contacting the sample from step (5) with a substrate conjugate comprised of a labeled substrate, where the substrate and label are linked optionally with a releasable linker;
(7) optionally removing unbound substrate conjugate;
(8) optionally deactivating the bound enzyme;
(9) optionally imaging the sample to detect the bound detectable labels; and
(10) optionally repeating steps (1)-(9) or any subset thereof.

Item 28. The method of item 27, further comprising (11) optionally releasing the bound detectable labels after step (9) by cleaving the releasable linker between the label and the substrate, and optionally repeating any of steps (1)-(9) and (11).

Item 29. A method for testing a sample for the presence of one or more targets comprising
(1) contacting a sample being tested for the presence of one or more targets with one or more target-specific binding partners, wherein each target-specific binding partner is linked to a nucleic acid strand and wherein target-specific binding partners of different specificity are linked to different nucleic acid strands;
(2) optionally removing unbound target-specific binding partners;
(3) contacting the sample from step (1) or optionally step (2) with an enzyme linked to a nucleic acid strand complementary to the nucleic acid strand linked to the target-specific binding partner
(4) optionally removing unbound enzyme linked to complementary nucleic acid strands;
(5) contacting the sample from step (3) or optionally step (4) with a substrate conjugate comprised of a nucleic acid strand-bound substrate, where the substrate and nucleic acid strand are linked optionally with a first releasable linker;
(6) optionally removing unbound substrate conjugates;
(7) optionally deactivating the bound enzymes;
(8) contacting the sample from step (5) or optionally steps (6)-(7) with a nucleic acid strand bound detectable label, linked optionally with a second releasable linker, where the nucleic acid strand is a specific binding pair member to the nucleic acid strand in step (5);
(9) optionally imaging the sample to detect the bound labels;
(10) optionally releasing the bound label from step (8) by releasing the linker of step (5) or optionally step (8) or optionally steps (5) and (8); and
(11) optionally repeating steps (1)-(10) or any subset thereof.

Item 30. A method for testing a sample for the presence of one or more targets comprises
(1) contacting a sample being tested for the presence of one or more targets with one target-specific binding partner, wherein the target-specific binding partner is linked to a nucleic acid strand;
(2) optionally removing unbound target-specific binding partners,
(3) contacting the sample with HRP-bound nucleic acid strand, complementary to the nucleic acid strand linked to the target-specific binding partner;
(4) optionally removing unbound enzyme linked to complementary nucleic acid strands;
(5) contacting the sample from step (3) or optionally step (4) with a substrate conjugate comprised of a detectably labeled phenol-including substrate, where the substrate and the detectable label are linked optionally with a releasable linker;
(6) optionally removing unbound substrate;
(7) optionally imaging the sample to detect the bound detectable labels;
(8) optionally deactivating the HRP; and
(9) optionally repeating a subset of steps (1)-(8).

Item 31. The method of any one of items 26-30, wherein the enzyme is deactivated using dithiothreitol (DTI), tris(2-carboxyethyl)phosphine (TCEP), a reduced glutathione, a peroxide, a cyanide, a fluoride or an azide.

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

What is claimed is:
1. A method for testing a sample for the presence of one or more targets comprising:
(1) contacting a sample being tested for the presence of one or more targets with one or more target-specific binding partners, wherein each target-specific binding partner is linked to a nucleic acid strand and wherein target-specific binding partners of different specificity are linked to different nucleic acid strands;

(2) optionally removing unbound target-specific binding partners;

(3) contacting the sample from step (1) or optionally step (2) with an enzyme linked to a nucleic acid strand complementary to the nucleic acid strand linked to the target-specific binding partner (4) optionally removing unbound enzyme linked to complementary nucleic acid strands;

(5) contacting the sample from step (3) or optionally step (4) with a substrate conjugate comprised of a nucleic acid strand-bound substrate, where the substrate and nucleic acid strand are linked optionally with a first releasable linker;

(6) optionally removing unbound substrate conjugates;

(7) optionally deactivating the bound enzymes or releasing the bound enzymes;

(8) contacting the sample from step (5) or optionally steps (6)-(7) with a nucleic acid strand bound detectable label, linked optionally with a second releasable linker, where the nucleic acid strand is a specific binding pair member to the nucleic acid strand in step (5), and wherein either or both the first and second releasable linkers are present;

(9) imaging the sample to detect the bound labels;

(10) releasing the bound label by releasing the first releasable linker or the second releasable linker or both; and

(11) optionally repeating steps (1)-(10) or any subset thereof and optionally if more than one target-specific binding partner is used, repeating steps (1)-(8) or any subset thereof prior to step (9) of imaging.

2. The method of claim 1, (3) wherein in step (3) the following (i) or (ii) or both is met:

(i) the nucleic acid strand is linked to the target-specific binding partner with a third releasable linker; and (ii) the enzyme is linked to the complimentary complementary nucleic acid strand with a fourth releasable linker.

3. The method of claim 1, wherein the bound label is released by dehybridization of the nucleic acid strand from step (8) bound to the nucleic acid strand from step (5).

4. The method of claim 1, wherein the method further comprises amplifying the nucleic acid strand or a portion thereof of the nucleic acid strand-bound substrate of step (5), optionally wherein the amplifying step is performed after step (5) or optional step (6) or optional step (7).

5. The method of claim 1, wherein step (11) is performed.

6. The method of claim 1, wherein the enzyme is horseradish peroxidase (HRP) and the substrate is a phenolic substrate.

7. The method of claim 1, wherein the enzyme is deactivated using an enzyme deactivator, wherein the enzyme deactivator comprises tris(2-carboxyethyl)phosphine (TCEP), dithiothreitol (DTT), a reduced glutathione, a peroxide, a cyanide, a fluoride, or an azide.

8. The method of claim 1, wherein in step (5), the substrate conjugate comprised of the nucleic acid strand-bound substrate reacts with the enzyme to form an activated substrate conjugate, and the activated substrate conjugate binds to a receptor for the activated substrate conjugate.

9. The method of claim 8, wherein the receptor for the activated substrate conjugate is present in the sample, resulting in the deposition of the nucleic acid strand-bound substrates.

10. The method of claim 1, wherein the method further comprises amplifying the nucleic acid strand or a portion thereof linked to the target-specific binding partner of step (1).

11. The method of claim 1, further comprising after steps (9) and (10), repeating steps of (1)-(8) or a subset thereof for detection of more targets.

12. The method of claim 1, further comprising repeating steps (3)-(8) or a subset thereof prior to step (9) of imaging for detection of more targets.

13. The method of claim 1, wherein the method further comprises repeating steps (3)-(8) or a subset thereof prior to step (9) of imaging; and wherein after steps (9) and (10), the method comprises repeating steps (1)-(8) or a subset thereof for detection of more targets.

14. A method for testing a sample for the presence of one or more targets comprising:

(1) contacting a sample being tested for the presence of one or more targets with one or more target-specific binding partners, wherein each target-specific binding partner is linked to a nucleic acid strand and wherein target-specific binding partners of different specificity are linked to different nucleic acid strands;

(2) optionally removing unbound target-specific binding partners;

(3) contacting the sample from step (1) or optionally step (2) with an enzyme linked to a nucleic acid strand complementary to the nucleic acid strand linked to a first target-specific binding partner;

(4) optionally removing unbound enzyme linked to complementary nucleic acid strands;

(5) contacting the sample from step (3) or optionally step (4) with a substrate conjugate comprised of a nucleic acid strand-bound substrate, where the substrate and nucleic acid strand are linked with a first releasable linker;

(6) optionally removing unbound substrate conjugates;

(7) deactivating the bound enzymes or releasing the bound enzymes;

(8) optionally repeating steps (3)-(7) for a next target-specific binding partner, resulting in two or more distinct substrate conjugates bound to the sample;

(9) contacting the sample from step (8) with one or more nucleic acid strand bound detectable labels, wherein each nucleic acid strand and detectable label are linked with a second releasable linker, and each nucleic acid stand is a specific binding pair member to the nucleic acid strand of the substrate conjugate specific for the same target-specific binding partner,

(10) imaging the sample to detect the bound labels;

(11) optionally releasing the bound labels from step (8) by releasing the first releasable linker or the second releasable linker or both;

(12) optionally repeating steps (1)-(11) or any subset thereof.

* * * * *

UNITED STATES PATENT AND TRADEMARK OFFICE
CERTIFICATE OF CORRECTION

| | |
|---|---|
| PATENT NO. | : 11,761,955 B2 |
| APPLICATION NO. | : 16/433621 |
| DATED | : September 19, 2023 |
| INVENTOR(S) | : Mark Bobrow, Stephanie Hennek and Mael Manesse |

It is certified that error appears in the above-identified patent and that said Letters Patent is hereby corrected as shown below:

In the Claims

In Claim 2, Column 37, Line 40, delete "complimentary"

Signed and Sealed this
Fourteenth Day of November, 2023

Katherine Kelly Vidal
*Director of the United States Patent and Trademark Office*